US006586658B1

(12) United States Patent
Peoples et al.

(10) Patent No.: US 6,586,658 B1
(45) Date of Patent: Jul. 1, 2003

(54) MODIFICATION OF FATTY ACID METABOLISM IN PLANTS

(75) Inventors: Oliver P. Peoples, Arlington, MA (US); Maurice Moloney, Calgary (CA); Nii Patterson, Calgary (CA); Kristi D. Snell, Belmont, MA (US)

(73) Assignee: Metabolix, Inc., Cambridge, MA (US)

( * ) Notice: Subject to any disclaimer, the term of this patent is extended or adjusted under 35 U.S.C. 154(b) by 0 days.

(21) Appl. No.: 09/389,395

(22) Filed: Sep. 3, 1999

Related U.S. Application Data

(63) Continuation-in-part of application No. 09/263,406, filed on Mar. 5, 1999.
(60) Provisional application No. 60/077,107, filed on Mar. 6, 1998.

(51) Int. Cl.[7] .............................. A01H 1/00; C12Q 1/68; C12N 15/82; C12N 15/87; C07H 21/04
(52) U.S. Cl. ...................... 800/281; 435/6; 435/91.1; 435/468; 536/23.2; 536/23.6; 800/278; 800/298
(58) Field of Search ....................... 435/6, 69.1, 91.1, 435/468, 471, 375; 536/23.1; 800/278, 281, 288, 294

(56) References Cited

U.S. PATENT DOCUMENTS

| | | |
|---|---|---|
| 5,004,863 A | 4/1991 | Umbeck |
| 5,015,580 A | 5/1991 | Christou et al. |
| 5,015,944 A | 5/1991 | Bubash |
| 5,024,944 A | 6/1991 | Collins et al. |
| 5,030,572 A | 7/1991 | Power et al. |
| 5,034,322 A | 7/1991 | Rogers et al. |
| 5,169,770 A | 12/1992 | Chee et al. |
| 5,188,958 A | 2/1993 | Moloney et al. |
| 5,229,279 A | 7/1993 | Peoples et al. |
| 5,231,019 A | 7/1993 | Paszkowski et al. |
| 5,245,023 A | 9/1993 | Peoples et al. |
| 5,268,463 A | 12/1993 | Jefferson |
| 5,276,268 A | 1/1994 | Strauch et al. |
| 5,322,783 A | 6/1994 | Tomes et al. |
| 5,364,780 A | 11/1994 | Hershey et al. |
| 5,384,253 A | 1/1995 | Krzyzek et al. |
| 5,416,011 A | 5/1995 | Hinchee et al. |
| 5,420,034 A | 5/1995 | Kridl et al. |
| 5,464,765 A | 11/1995 | Coffee et al. |
| 5,480,794 A | 1/1996 | Peoples et al. |
| 5,502,273 A | 3/1996 | Bright et al. |
| 5,519,164 A | 5/1996 | Mullner et al. |
| 5,527,695 A | 6/1996 | Hodges et al. |
| 5,530,196 A | 6/1996 | Fraley et al. |
| 5,538,877 A | 7/1996 | Lundquist et al. |
| 5,545,818 A | 8/1996 | McBride et al. |
| 5,602,321 A | 2/1997 | John |
| 5,608,152 A | 3/1997 | Kridl et al. |
| 5,610,041 A | 3/1997 | Somerville et al. |
| 5,629,183 A | 5/1997 | Saunders et al. |
| 5,650,554 A | 7/1997 | Moloney |
| 5,668,298 A | 9/1997 | Waldron |
| 6,091,002 A | * 7/2000 | Asrar et al. ................ 800/288 |

FOREIGN PATENT DOCUMENTS

| | | |
|---|---|---|
| DE | 195 31 678 A1 | 3/1997 |
| EP | 0 486 233 A2 | 5/1992 |
| EP | 0 530 129 A1 | 3/1993 |
| EP | 0 604 662 A1 | 7/1994 |
| EP | 0 894 864 A1 | 2/1999 |
| WO | WO 91/00917 A1 | 1/1991 |
| WO | WO 92/19747 A1 | 11/1992 |
| WO | WO 93/02187 A1 | 2/1993 |
| WO | WO 93/02194 A1 | 2/1993 |
| WO | WO 93/20216 A1 | 10/1993 |
| WO | WO 94/00977 A1 | 1/1994 |
| WO | WO 94/12014 A1 | 6/1994 |
| WO | WO 94/23027 A2 | 10/1994 |
| WO | WO 95/20614 A1 | 8/1995 |
| WO | WO 95/20615 A1 | 8/1995 |
| WO | WO 95/20621 A1 | 8/1995 |
| WO | WO 97 10703 A1 | 3/1997 |
| WO | WO 97/15681 A1 | 5/1997 |
| WO | WO 98/00557 A2 | 1/1998 |
| WO | WO 98/06831 A1 | 2/1998 |
| WO | WO 98/06854 A1 | 2/1998 |

OTHER PUBLICATIONS

Abe, et al., "Biosynthesis from gluconate of a random copolyester consisting of 3–hydroxybutyrate and medium–chain–length 3–hydroxyalkanoates by Pseudomonas sp. 61–3," *Int. J. Biol. Macromol.* 16:115–19 (1994).

Andrews, et al., "Fatty acid and lipid biosynthesis and degradation" in *Plant Physiology, Biochemistry, and Molecular Biology* (Dennis et al., eds.) pp. 345–346 (Longman Scientific & Technical, Essex, England 1990).

Bedwell, et al., "Sequence and structural requirements of a mitochondrial protein import signal defined by saturation cassette mutagenesis," *Mol Cell Biol.* 9(3):1014–25 (1989).

Binstock & Schulz, "Fatty acid oxidation complex from *Escherichia coli*," *Methods in Enzymol.* 71 Pt C:403–11 (1981).

(List continued on next page.)

*Primary Examiner*—Ram R. Shukla
*Assistant Examiner*—Jane Zara
(74) *Attorney, Agent, or Firm*—Holland & Knight LLP

(57) ABSTRACT

Methods and systems to modify fatty acid biosynthesis and oxidation in plants to make new polymers are provided. Two enzymes are essential: a hydratase such as D-specific enoyl-CoA hydratase, for example, the hydratase obtained from *Aeromonas caviae*, and a β-oxidation enzyme system. Some plants have a β-oxidation enzyme system which is sufficient to modify polymer synthesis when the plants are engineered to express the hydratase. Examples demonstrate production of polymer by expression of these enzymes in transgenic plants. Examples also demonstrate that modifications in fatty acid biosynthesis can be used to alter plant phenotypes, decreasing or eliminating seed production and increasing green plant biomass, as well as producing polyhydroxyalkanoates.

26 Claims, 12 Drawing Sheets-

OTHER PUBLICATIONS

Brickner, et al., "Protein transport into higher plant peroxisomes. In vitro import assay provides evidence for receptor involvement," *Plant Physiol.* 113(4):1213–21 (1997).

Cevallos, et al., "Genetic and physiological characterization of a Rhizobium etli mutant strain unable to synthesize poly–beta–hydroxybutyrate," *J Bacteriol.* 178(6):1646–54 (1996).

Cubitt, et al., "Understanding, improving and using green fluorescent proteins," *Trends Biochem Sci.* 20(11):448–55 (1995).

Dale & Ow, "Gene transfer with subsequent removal of the selection gene from the host genome," *Proc Natl Acad Sci U S A.* 88(23):10558–62 (1991).

Deng, et al., "Expression of soybean–embryo lipoxygenase–2 in transgenic tobacco tissue," *Plants* 187:203–208 (1992).

Dirusso, "Primary sequence of the *Escherichia coli* fadB operon, encoding the fatty acid–oxidizing multienzyme complex, indicates a high degree of homology of eucaryotic enzymes," *J Bacteriol.* 172(11):6459–68 (1990).

Filppula, et al., "Changing stereochemistry for a metabolic pathway in vivo. Experiments with the peroxisomal beta–oxidation in yeast," *J Biol Chem.* 270(46):27453–57 (1995).

Fromm, et al., "Inheritance and expression of chimeric genes in the progeny of transgenic maize plants," *Biotechnology (N Y).* 8(9):833–39 (1990).

Fukui & Doi, "Cloning and analysis of the poly(3–hydroxybutyrate–co–3–hydroxyhexaonoate) biosynthesis genes of *Aeromonas ceviae*," *J Bacteriol.* 179(15):4821–30 (1997).

Fukui, et al., "Expression and characterization of (R)–specific enoyl coenzyme A hydratase involved in polyhydroxyalkanoate biosynthesis by *Aeromonas caviae*," *J Bacteriol.* 180(3):667–73 (1998).

Gasser & Fraley, "Genetically Engineering Plants for Crop Improvement," *Science* 244:1293–1299 (1989).

Gerhardt, "Catabolism of Fatty Acids [α and β Oxidation]" in *Lipid Metabolism in Plants* (Moore, Jr., ed.) pp. 527–65 (CRC Press, Boca Raton, Florida 1993).

Gould, et al., "A conserved tripeptide sorts proteins to peroxisomes," *J Cell Biol.* 108(5):1657–64 (1989).

Hall, et al., "Cloning of the Nocardia corallina polyhydroxyalkanoate gene and production of poly–(3–hydroxybutyrate–co–3–hydroxyhexanoate) and poly–(3–hydroxyvalerate–co–3–hydroxyheptanoate)," *Can J Microbiol.* 44(7):687–91 (1998).

Harwood, "Plant Lipid Metabolism" in *Plant Biochemistry* (Dey et al., eds) p. 246–272 (Academic Press:San Diego, 1997).

Haywood, et al., "Characterization of two 3–ketothiolases possessing differing substrate specificites in the polyhydroxyalkanoate synthesizing organism *Alcaligenes eutrophus*," *FEMS Micro. Lett.* 52:91–96 (1988).

He & Yang, "Glutamate–119 of the large alpha–subunit is the catalytic base in the hydration of 2–trans–enoyl–coenzyme A catalyzed by the multienzyme complex of fatty acid oxidation from *Escherichia coli*," *Biochemistry.* 36(36):11044–49 (1987).

He & Yang, "Histidine–450 is the catalytic residue of L–3–hydroxyacyl coenzyme A dehydrogenase associated with the large alpha–subunit of the multienzyme complex of fatty acid oxidation from *Escherichia coli*," *Biochemistry.* 35(29):9625–30 (1996).

He, et al., "Importance of the gamma–carboxy group of glutamate–462 of the large alpha–subunit for the catalytic function and the stability of the multienzyme complex of fatty acid oxidation from *Escherichia coli*," *Biochemistry.* 36(1):261–68 (1997).

Hiltunen, et al., "Peroxisomal multifunctional beta–oxidation protein of Saccharomyces cerevisiae. Molecular analysis of the fox2 gene and gene product," *J Biol Chem.* 267(10):6646–53 (1992).

Hood, et al., "The hypervirulence of Agrobacterium tumefaciens A281 is encoded in a region of pTiBo542 outside of T–DNA," *J Bacteriol.* 168(3):1291–301 (1986).

Horwich, "Protein import into mitochondria and peroxisomes," *Curr Opin Cell Biol.* 2(4):625–33 (1990).

Huijberts, et al., "13c nuclear magnetic resonance studies of *Pseudomonas putida* fatty acid metabolic routs involved in poly(3–hydroxyalkanoate) synthesis," *J. Bacteriol.* 176:1661–66 (1994).

Huisman, et al., "Metabolism of poly(3–hydroxyalkanoates) (PHAs) by Pseudomonas oleovorans. Identification and sequences of genes and function of the encoded proteins in the synthesis and degradation of PHA," *J. Biol. Chem.* 266(4):2191–98 (1991).

Hustede, et al., "Cloning of poly(3–hydroxybutyric acid) synthase genes of *Rhodobacter sphaeroides* and *Rhodospirillum rubrum* and heterologous expression in *Alcaligenes eutrophus*," *FEMS Microbiol. Lett* 93:285–90 (1992).

Imamura, et al., "Purification of the multienzyme complex for fatty acid oxidation from *Pseudomonas fragi* and reconstitution of the fatty acid oxidation system," *J Biochem* 107(2):184–89 (1990).

Ishikawa, et al., "Reconstitution morphology and crystallization of a fatty acid beta–oxidation multienzyme complex from *Pseudomonas fragi*," *Biochemical Journal* 328:815–20 (1997).

Jefferson, et al., "GUS fusions: β–glucuronidase as a sensitive and versatile gene fusion marker in higher plants," *EMBO J.* 6(13):3901–907 (1987).

Kaneko, et al., "Sequence analysis of the genome of the unicellular cyanobacterium Synechocystis sp. strain PCC6803. II. Sequence determination of the entire genome and assignment of potentia protein–coding regions," *DNA Res.* 3(3):109–35 (1996).

Kato, et al., "Production of a novel copolyester of 3–hydroxybutyric acid with a medium–chain–length 3–hydroxyalkanoic acids by Pseudomonas sp. 61–3 from sugars," *Appl. Microbiol. Biotechnol.* 45:363–70 (1996).

Kyozuka, et al., "Anaerobic induction and tissue–specific expression of maize Adh1 promoter in transgenic rice plants and their progeny," *Mol Gen Genet.* 228(1–2):40–8 (1991).

Lee, et al., "Biosynthesis of copolyesters consisting of 3–hydroxybutyric aicd and medium chain length 3–hydroxyalkanoic acids from 1,3–butanediol or from 3–hydroxybutyrate by Pseudomonas sp. A33," *Appl. Microbiol. Biotechnol.* 42:901–909 (1995).

Liebergesell & Steinbüchel, "Cloning and molecular analysis of the poly(3–hydroxybutyric acid) biosynthetic genes of *Thiocystis violacea*," *Appl Microbiol Biotechnol.* 38(4):493–501 (1993).

Liebersgesell & Steinbüchel, "Cloning and nucleotide sequences of genes relevant for biosynthesis of poly(3–hydroxybutyric acid) in *Chromatium vinosum* strain D," *European J. Biochem.* 209:135–50 (1992).

Maliga, et al., *Methods in Plant Molecular Biology: A Laboratory Course Manual* Cold Spring Laboratory Press: New York, 1995.

Matsusaki, et al., "Cloning and molecular analysis of the poly(3–hydroxybutyrate) and poly(3–hydroxybutyrate–co–3–hydroxyalkanoate) biosynthesis genes in Pseudomonas sp. strain 61–3," *J Bacteriol.* 180(24):6459–67 (1998).

McElroy, et al., "Isolation of an efficient actin promoter for use in rice transformation," *Plant Cell.* 2(2):163–71 (1990).

Medberry, et al., "Intra–chromosomal rearrangements generated by Cre–lox site–specific recombination," *Nucleic Acids Res.* 23(3):485–90 (1995).

Millar, et al., "Accumulation of very–long–chain fatty acids in membrane gycerolipids is associated with dramatic alterations in plant morphology," *The Plant Cell* 11:1889–902 (1998).

Moloney, et al., "High efficiency transformation of *Brassica napus* Agrobacterium vectors," *Plant Cell Reports* 8:238–42 (1989).

Nawrath & Poirier, "Review on polyhydroxyalkanoate formation in the model plant *Arabidopsis thaliana*" in *The International Symposium on Bacterial Polyhydroxyalkanoates*, (Eggink et al., eds.) (Davos Switzerland, 1996).

Odell, et al., "Identification of DNA sequences required for activity of the cauliflower mosaic virus 35S promoter," *Nature.* 313(6005):810–12 (1985).

Olesen, et al., "The glyoxysomal 3–ketoacy–CoA thiolase precursor from *Brassica napus* has enzymatic activity when synthesized in *Escherichia coli*," *FEBS Letters* 412:138–140 (1997).

Owen, et al., *Transgenic Plants: A Production System for Industrial and Pharmaceutical Proteins* John Wiley & Sons Ltd.:England, 1996.

Palmer, et al., "Purification and complete sequence determination of the major plasma membrane substrate for cAMP–dependent protein kinase and protein kinase C in myocardium," *J Biol Chem.* 266(17):11126–30 (1991).

Palosaari & Hiltunen, "Peroxisomal bifunctional protein from rat liver is a trifunctional enzyme possessing 2–enoyl–CoA hydratase, 3–hydroxyacyl–CoA dehydrogenase, and delta 3, delta 2–enoyl–CoA isomerase activities," *J Biol Chem.* 265(5):2446–49 (1990).

Pang, et al., "An Improved green fluorescent protein gene as a vital marker in plants," *Plant Physiol.* 112:893–900 (1996).

Peoples & Sinskey, "Fine structural analysis of the *Zoogloea ramigera* phbA–phbB locus encoding β–ketothiolase and acetoacetyl–CoA reductase: nucleotide sequence of phbB," *Molecular Microbiol.* 3(3):349–57 (1989).

Peoples & Sinskey, "Poly–β–hydroxybutryte (PHB) Biosynthesis in *Alcaligenes eutrophus* H16," *J. Biol. Chem.* 264(26):15298–303 (1989).

Peoples, et al., "Biosynthetic Thiolase from *Zoogloea remigera*," *J. Biol. Chem.* 262(1):97–102 (1987).

Pieper & Steinbüchel, "Identification, cloning and sequence analysis of the poly(3–hydroxyalkanoic acid) synthase gene of the gram–positive bacterium *Rhodococcus ruber*," *FEMS Microbiol Lett.* 75(1):73–80 (1992).

Plant, et al., "Regulation of an Arabidopsis oleosin gene promoter in transgenic *Brassica napus*," *Plant Mol Biol.* 25(2):193–205 (1994).

Poirier, et al., "Polyhydroxybutyrate, a Biodegradable Thermoplastic, Produced in Transgenci Plants," *Science* 256:520–23 (1992).

Potyrykus & Spangenberg, *Gene Transfer to Plants* (Springer–Verlag:Berlin Heidelberg New York, 1995.)

Preisig–Müller, et al., "Domains of the tetrafunctional protein acting in glyoxysomal fatty acid beta–oxidation. Demonstration of epimerase and isomerase activities on a peptide lacking hydratase activity," *J Biol Chem.* 269(32):20475–81 (1994).

Rowley & Herman, "The upstream domain of soybean oleosin genes contains regulatory elements similar to those of legume storage proteins," *Biochim Biophys Acta.* 1345(1):1–4 (1997).

Sambrook, et al., *Molecular Cloning: a laboratory manual*, (2nd Ed.), Cold Spring Harbor Laboratory Press:Cold Spring Harbor, NY, 1992.

Sato, et al., "Primary structures of the genes, faoA and faoB, from *Pseudomonas fragi* B–0771 which encode the two subunits of the HDT multienzyme complex involved in fatty acid beta–oxidation," *J Biochem.* 111(1):8–15 (1992).

Schembri, et al., "Cloning and analysis of the polyhydroxyalkanoic acid synthase gene from an Acinetobacter sp.: evidence that the gene is both plasmid and chromosomally located," *FEMS Microbiol Lett.* 118(1–2):145–52 (1994).

Schultz, et al., "Oxidation of Fatty Acids" in *Biochemistry of Lipids, Lipoproteins and Membranes* (Vance et al., eds.) pp. 101–106, (Elsevier:Amsterdam, 1991).

Slightom, et al., "Complete nucleotide sequence of a French bean storage protein gene: Phaseolin," *Proc. Natl. Acad. Sci. USA* 80:1897–901 (1983).

Small, et al., "Acyl–CoA oxidase contains two targeting sequences each of which can mediate protein import into peroxisomes," *EMBO J.* 7(4):1167–73 (1988).

Smeland, et al., "The 3–hydroxyacyl–CoA epimerase activity of rat liver peroxisomes is due to the combined actions of two enoyl–CoA hydratases: a revision of the epimerase–dependent pathway of unsaturated fatty acid oxidation," *Biochem Biophys Res Commun.* 160(3):988–92 (1989).

Spratt, et al., "Cloning, mapping, and expression of genes involved in the fatty acid–degradative multienzyme complex of *Escherichia coli*," *J Bacteriol.* 158(2):535–42 (1984).

Steinbüchel & Wiese, "A Pseudomonas strain accumulating polyesters of 3–hydroxybutyric acid and medium–chain–length 3–hydroxyalkanoic acids," *Appl. Microbiol. Biotechnol.* 37:691–97 (1992).

Steinbüchel, et al., "Molecular basis for biosynthesis and accumulation of polyhydroxyalkanoic acids in bacteria," *FEMS Microbiol Rev.* 9(2–4):217–30 (1992).

Timm & Steinbüchel, "Cloning and molecular analysis of the poly(3–hydroxyalkanoic acid) gene locus of *Pseudomonas aeruginosa* PAO1," *Eur J Biochem.* 209(1):15–30 (1992).

Tombolini, et al., "Poly–beta–hydroxybutyrate (PHB) biosynthetic genes in Rhizobium meliloti 41," *Microbiology.* 141 (Pt 10):2553–59 (1995).

Ueda, et al., "Molecular analysis of the poly(3–hydroxyalkaoate) synthase gene from a methylotrophic bacterium, Paracoccus denitrificans," *J Bacteriol.* 178(3):774–79 (1996).

Umeda, et al., "Cloning and sequence analysis of the poly (3–hydroxyalkanoic acid)–synthesis genes of Pseudomonas acidophila," *Appl Biochem Biotechnol.* 70–72:341–52 (1998).

Valentin & Steinbüchel "Cloning and characterization of the Methylobacterium extorquens polyhydroxyalkanoic–acid–synthase structural gene," *Appl Microbiol Biotechnol.* 39(3):309–17 (1993).

Valentin, et al., "Identification of 4–hydroxyhexanoic acid as a new constituent of biosynthetic polyhydroxyalkanoic acids from bacteria," *Appl. Microbiol. Biotechnol.* 40:710–16 (1994).

Valentin, et al., "Identification of 4–hydroxyvaleric acid as a constituent of biosynthetic polyhydroxyalkanoic acids from bacteria," *Appl. Microbiol, Biotechnol.* 36: 507–14 (1992).

Valentin, et al., "Identification of 5–hydroxyhexanoic acid, 4–hydroxyheptanoic acid and 4–hydroxyoctanoic acid as new constituents of bacterial polyhydroxyalkanoic acids," *Appl. Microbiol. Biotechnol.* 41:261–67 (1995).

van der Leij & Witholt, "Strategies for the sustainable production of new biodegradable polyesters in plants: a review," *Can. J. Microbiol.* 41(supplement):222–38 (1995).

Vollack & Bach, "Cloning of a cDNA encoding cytosolic acetoacetyl–coenzyme A thiolase from radish by functional expression in *Saccharomyces cerevisiae*," *Plant Physiol.* 111(4):1097–107 (1996).

Williams & Peoples, "Biodegradable plastics from plants," *ChemTech* 26:38–44 (1996).

Yabutani, et al., "Analysis of beta–ketothiolase and acetoacetyl–CoA reductase genes of a methylotrophic bacterium, Paracoccus denitrificans, and their expression of *Escherichia coli*," *FEMS Microbiol Lett.* 133(1–2):85–90 (1995).

Yang & Elzinga, "Association of both enoyl coenzyme A epimerase with an active site in the amino–terminal domain of the multifunctional fatty acid oxidation protein from *Escherichia coli*," *J Biol Chem.* 269(9):6588–92 (1993).

Yang, et al., "Glutamate 139 of the large alpha–subunit is the catalytic base in the dehydration of both D–and L–3–hydroxyacyl–coenzyme A but not in the isomerization of delta 3, delta 2–enoyl–coenzyme A catalyzed by the multienzyme complex of fatty acid oxidation from *Escherichia coli*," *Biochemistry.* 34(19):6441–47 (1995).

\* cited by examiner

MODIFICATION OF FATTY ACID METABOLISM IN PLANTS

CROSS-REFERENCE TO RELATED APPLICATIONS

This application is a C-I-P of U.S. application Ser. No. 09/263,406, filed Mar. 5, 1999, which claims priority to U.S. Provisional application Serial No. 60/077,107, filed Mar. 6, 1998.

BACKGROUND OF THE INVENTION

The present invention is generally in the field of transgenic plant systems for the production of polyhydroxyalkanoate materials, modification of triglycerides and fatty acids, and methods for altering seed production in plants.

Methods for producing stable transgenic plants for agronomic crops have been developed over the last 15 years. Crops have been genetically modified for improvements in both input and output traits. In the former traits, tolerance to specific agrochemicals has been engineered into crops, and specific natural pesticides, such as the *Bacillus thuringenesis* toxin, have been expressed directly in the plant. There also has been significant progress in developing male sterility systems for the production of hybrid plants. With respect to output traits, crops are being modified to increase the value of the product, generally the seed, grain, or fiber of the plant. Critical metabolic targets include the modification of starch, fatty acid, and oil biosynthetic pathways.

There is considerable commercial interest in producing microbial polyhydroxyalkanoate (PHA) biopolymers in plant crops. See, for example, U.S. Pat. Nos. 5,245,023 and 5,250,430 to Peoples and Sinskey; U.S. Pat. No. 5,502,273 to Bright et al.; U.S. Pat. No. 5,534,432 to Peoples and Sinskey; U.S. Pat. No. 5,602,321 to John; U.S. Pat. No. 5,610,041 to Somerville et al.; PCT WO 91/00917; PCT WO 92/19747; PCT WO 93/02187; PCT WO 93/02194; PCT WO 94/12014; Poirier et al., *Science* 256:520–23 (1992); van der Leij & Witholt, *Can. J. Microbiol.* 41(supplement): 222–38 (1995); Nawrath & Poirier, *The International Symposium on Bacterial Polyhydroxyalkanoates,* (Eggink et al., eds.) Davos Switzerland (Aug. 18–23, 1996); Williams and Peoples, CHEMTECH 26: 38–44 (1996), and the recent excellent review by Madison, L. and G. Husiman, Microbiol. Mol. Biol. 21–53 (March 1999). PHAs are natural, thermoplastic polyesters and can be processed by traditional polymer techniques for use in an enormous variety of applications, including consumer packaging, disposable diaper linings and garbage bags, food and medical products.

Early studies on the production of polyhydroxybutyrate in the chloroplasts of the experimental plant system *Arabidopsis thaliana* resulted in the accumulation of up to 14% of the leaf dry weight as PHB (Nawrath et al., 1993). Arabidopsis, however, has no agronomic value. Moreover, in order to economically produce PHAs in agronomic crops, it is desirable to produce the PHAs in the seeds, so that the current infrastructure for harvesting and processing seeds can be utilized. The options for recovery of the PHAs from plant seeds (PCT WO 97/15681) and the end use applications (Williams & Peoples, CHEMTECH 26:38–44 (1996)) are significantly affected by the polymer composition. Therefore, it would be advantageous to develop transgenic plant systems that produce PHA polymers having a well-defined composition, as well as produce PHA polymer in specific locations within the plants and/or seeds.

Careful selection of the PHA biosynthetic enzymes on the basis of their substrate specificity allows for the production of PHA polymers of defined composition in transgenic systems (U.S. Pat. Nos. 5,229,279; 5,245,023; 5,250,430; 5,480,794; 5,512,669; 5,534,432; 5,661,026; and 5,663,063).

In bacteria, each PHA group is produced by a specific pathway. In the case of the short pendant group PHAs, three enzymes are involved: β-ketothiolase, acetoacetyl-CoA reductase, and PHA synthase. The homopolymer PHB, for example, is produced by the condensation of two molecules of acetyl-coenzyme A to give acetoacetyl-coenzyme A. The latter then is reduced to the chiral intermediate R-3-hydroxybutyryl-coenzyme A by the reductase, and subsequently polymerized by the PHA synthase enzyme. The PHA synthase notably has a relatively wide substrate specificity which allows it to polymerize C3–C5 hydroxy acid monomers including both 4-hydroxy and 5-hydroxy acid units. This biosynthetic pathway is found in a number of bacteria such as *Alcaligenes eutrophus, A. latus, Azotobacter vinlandii,* and *Zoogloea ramigera.* Long pendant group PHAs are produced for example by many different Pseudomonas bacteria. Their biosynthesis involves the β-oxidation of fatty acids and fatty acid synthesis as routes to the hydroxyacyl-coenzyme A monomeric units. The latter then are converted by PHA synthases which have substrate specificities favoring the larger C6–C14 monomeric units (Peoples & Sinskey, 1990).

In the case of the PHB-co-HX copolymers which usually are produced from cells grown on fatty acids, a combination of these routes can be responsible for the formation of the different monomeric units. Indeed, analysis of the DNA locus encoding the PHA synthase gene in *Aeromonas caviae,* which produces the copolymer PHB-co-3-hydroxyhexanoate, was used to identify a gene encoding a D-specific enoyl-CoA hydratase responsible for the production of the D-β-hydroxybutyryl-CoA and D-β-hydroxyhexanoyl-CoA units (Fukui & Doi, *J. Bacteriol.* 179:4821–30 (1997); Fukui et. al., *J. Bacteriol.* 180:667–73 (1998)). Other sources of such hydratase genes and enzymes include Alcaligenes, Pseudomonas, and Rhodospirillum.

The enzymes PHA synthase, acetoacetyl-CoA reductase, and β-ketothiolase, which produce the short pendant group PHAs in *A. eutrophus,* are coded by an operon comprising the phbC-phbA-phbB genes; Peoples et al., 1987; Peoples & Sinskey, 1989). In the Pseudomonas organisms, the PHA synthases responsible for production of the long pendant group PHAs have been found to be encoded on the pha locus, specifically by the phaA and phaC genes (U.S. Pat. Nos. 5,245,023 and 5,250,430; Huisman et. al., *J. Biol. Chem.* 266:2191–98 (1991)). Since these earlier studies, a range of PHA biosynthetic genes have been isolated and characterized or identified from genome sequencing projects. Known PHA biosynthetic genes include: *Aeronomas caviae* (Fukui & Doi, 1997, *J. Bacteriol.* 179:4821–30); *Alcaligenes eutrophus* (U.S. Pat. Nos. 5,245,023; 5,250,430; 5,512,669; and 5,661,026; Peoples & Sinskey, *J. Biol. Chem.* 264:15298–03 (1989)); Acinetobacter (Schembri et. al., *FEMS Microbiol. Lett.* 118:145–52 (1994)); *Chromatium vinosum* (Liebergesell & Steinbuchel, *Eur. J. Biochem.* 209:135–50 (1992)); *Methylobacterium extorquens* (Valentin & Steinbuchel, *Appl. Microbiol. Biotechnol.* 39:309–17 (1993)); *Nocardia corallina* (GENBANK Accession No. AF019964; Hall et. al., 1998, *Can. J. Microbiol.* 44:687–69); *Paracoccus denitrificans* (Ueda et al., *J. Bacteriol.* 17:774–79 (1996); Yabutani et. al., *FEMS Microbiol. Lett.* 133:85–90 (1995)); *Pseudomonas acidophila* (Umeda et. al., 1998, *Applied Biochemistry and Biotechnology,* 70–72:341–52); Pseudomonas sp. 61-3 (Matsusaki et al., 1998, *J. Bacteriol.* 180:6459–67); *Nocardia corallina; Pseudoinonas aeruginosa* (Timm & Steinbuchel, *Eur. J. Biochem.* 209:15–30 (1992)); *P. oleovorans* (U.S. Pat. Nos. 5,245,023 and 5,250,430; Huisman et. al., *J. Biol. Chem.* 266(4):2191–98 (1991); *Rhizobium etli* (Cevallos et. al., *J. Bacteriol.* 178:1646–54 (1996)); *R. meliloti* (Tombolini et. al., *Microbiology* 141:2553–59 (1995)); *Rhodococcus ruber* (Pieper-Furst & Steinbuchel, FEMS Microbiol. Lett. 75:73–79 (1992)); *Rhodospirillum rubrum* (Hustede et. al., *FEMS Microbiol. Lett* 93:285–90 (1992)); *Rhodobacter sphaeroides* (Hustede et. al., *FEMS Microbiol. Rev.* 9:217–30 (1992); *Biotechnol. Lett.* 15:709–14 (1993); Synechocystis sp. (*DNA Res.* 3:109–36 (1996)); *Thiocapsiae violacea* (*Appl. Microbiol. Biotechnol.* 3:493–501 (1993)) and *Zoogloea ramigera* (Peoples et. al., *J. Biol. Chem.* 262:97–102 (1987); Peoples & Sinskey, *Molecular Microbiology* 3:349–57 (1989)). The availability of these genes or their published DNA sequences should provide a range of options for producing PHAs.

PHA synthases suitable for producing PHB-co-HH copolymers comprising from 1–99% HH monomers are encoded by the *Rhodococcus ruber, Rhodospirillum rubrum, Thiocapsiae violacea,* and *Aeromonas caviae* PHA synthase genes. PHA synthases useful for incorporating 3-hydroxyacids of 6–12 carbon atoms in addition to R-3-hydroxybutyrate i.e. for producing biological polymers equivalent to the chemically synthesized copolymers described in PCT WO 95/20614, PCT WO 95/20615, and PCT WO 95/20621 have been identified in a number of Pseudomonas and other bacteria (Steinbuichel & Wiese, *Appl. Microbiol. Biotechnol.* 37:691–97 (1992); Valentin et al., *Appl. Microbiol. Biotechnol.* 6:507–14 (1992); Valentin et al., *Appl. Microbiol. Biotechnol.* 40:710–16 (1994); Lee et al., *Appl. Microbiol. Biotechnol.* 42:901–09 (1995); Kato et al., *Appl. Microbiol. Biotechnol.* 45:363–70 (1996); Abe et al., *Int. J. Biol. Macromol.* 16:115–19 (1994); Valentin et al., *Appl. Microbiol. Biotechnol.* 46:261–67 (1996)) and can readily be isolated as described in U.S. Pat. Nos. 5,245,023 and 5,250,430. The PHA synthase from *P. oleovorans* (U.S. Pat. Nos. 5,245,023 and 5,250,430; Huisman et. al., *J. Biol. Chem.* 266(4): 2191–98 (1991)) is suitable for producing the long pendant group PHAs. Plant genes encoding β-ketothiolase also have been identified (Vollack & Bach, *Plant Physiol.* 111:1097–107 (1996)).

Despite this ability to modify monomer composition by selection of the syntheses and substrates, it is desirable to modify other features of polymer biosynthesis, such as fatty acid metabolism.

It is therefore an object of the present invention to provide a method and DNA constructs to introduce fatty acid oxidation enzyme systems for manipulating the cellular metabolism of plants.

It is another object of the present invention to provide methods for enhancing the production of PHAs in plants, preferably in the oilseeds thereof.

SUMMARY OF THE INVENTION

Methods and systems to modify fatty acid biosynthesis and oxidation in plants to make new polymers are described. Two enzymes are essential: a hydratase such as D-specific enoyl-CoA hydratase, for example, the hydratase obtained from *Aeromonas caviae,* and a β-oxidation enzyme system. Some plants have a β-oxidation enzyme system which is sufficient to modify polymer synthesis when the plants are engineered to express the hydratase. Tissue specific and constitutive promoters were used to regulate and direct polymer production. Fusion constructs enhance polymer production.

Examples demonstrate production of polymer by expression of these enzymes in transgenic plants. Examples also demonstrate that modifications in fatty acid biosynthesis can be used to alter plant phenotypes, decreasing or eliminating seed production and increasing green plant biomass, as well as producing PHAs. Use of the phaseolin promoter can be used to induce male sterility. Tissue specific promoters in fusion constructs were used to modify production within regions of the seeds.

DETAILED DESCRIPTION OF THE INVENTION

Figure 1:
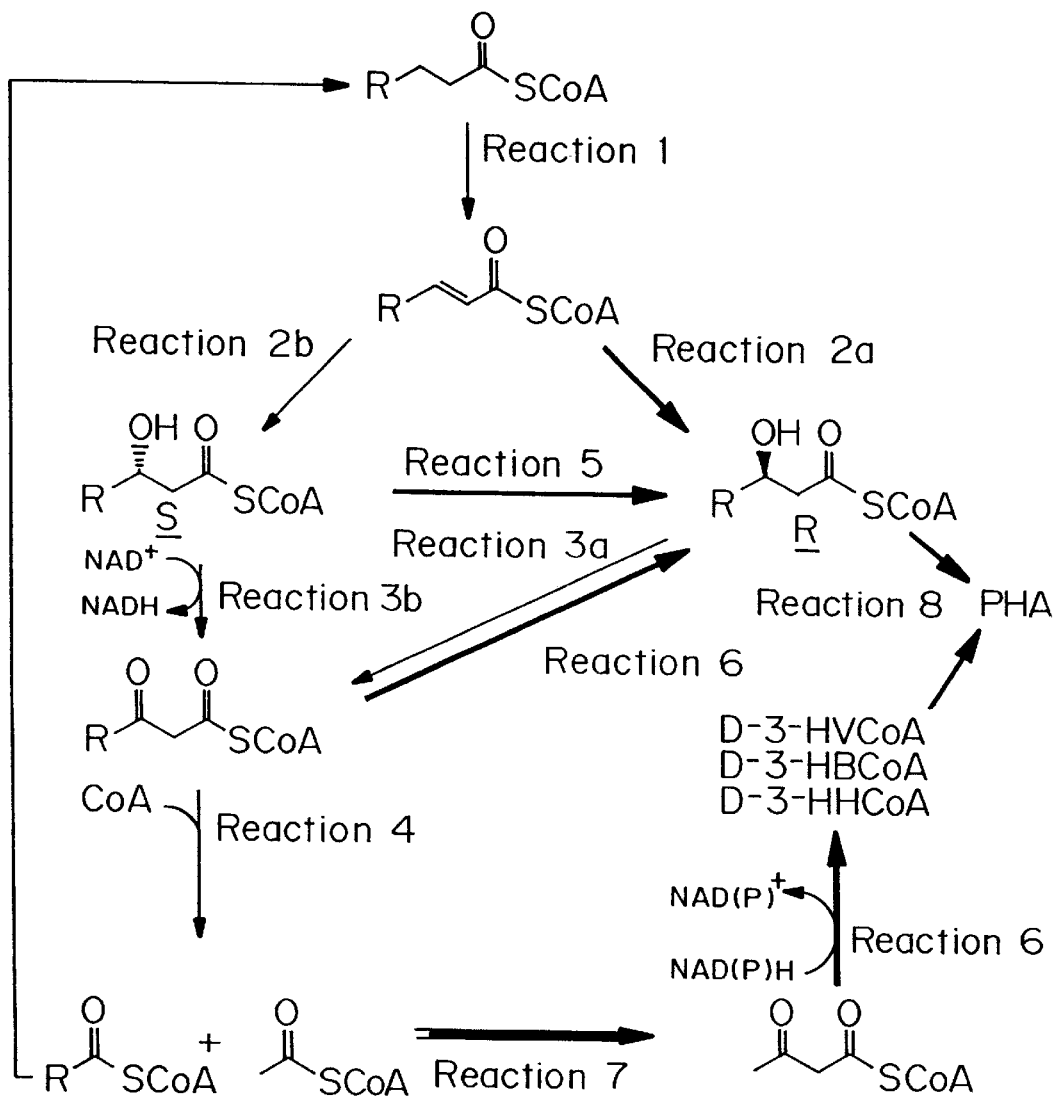
FIG. 1 is a schematic of fatty acid β-oxidation routes to produce polyhydroxyalkanoate monomers.

Methods and DNA constructs for manipulating the cellular metabolism of plants by introducing fatty acid oxidation enzyme systems into the cytoplasm or plastids of developing oilseeds or green tissue through the use of tissue specific and/or constitutive promoters, are provided. Fatty acid oxidation systems typically comprise several enzyme activities including a β-ketothiolase enzyme activity which utilizes a broad range of β-ketoacyl-CoA substrates.

It surprisingly was found that expression of at least one of these transgenes from the bean phaseolin promoter results in male sterility. Interestingly, these plants did not set seed, but instead produced higher than normal levels of biomass (e.g., leafs, stems, stalks). Therefore the methods and constructs described herein also can be used to create male sterile plants, for example, for hybrid production or to increase the production of biomass of forage, such as alfalfa or tobacco. Plants generated using these methods and DNA constructs are useful for producing polyhydroxyalkanoate biopolymers or for producing novel oil compositions.

The methods described herein include the subsequent incorporation of additional transgenes, in particular encoding additional enzymes involved in fatty acid oxidation or polyhydroxyalkanoate biosynthesis. For polyhydroxyalkanoate biosynthesis, the methods include the incorporation of transgenes encoding enzymes, such as NADH and/or NADPH acetoacetyl-CoenzymeA reductases, PHB synthases, PHA synthases, acetoacetyl-CoA thiolase, hydroxyacyl-CoA epimerases, delta3-cis-delta2-trans enoyl-CoA isomerases, acyl-CoA dehydrogenase, acyl-CoA oxidase and enoyl-CoA hydratases by subsequent transformation of the transgenic plants produced using the methods and DNA constructs described herein or by traditional plant breeding methods.

I. Plant Expression Systems

In a preferred embodiment, the fatty acid oxidation transgenes are expressed from a seed specific promoter, and the proteins are expressed in the cytoplasm of the developing oilseed. In an alternate preferred embodiment, fatty acid oxidation transgenes are expressed from a seed specific promoter and the expressed proteins are directed to the plastids using plastid targeting signals. In another preferred embodiment, the fatty acid oxidation transgenes are expressed directly from the plastid chromosome where they have been integrated by homologous recombination. The fatty acid oxidation transgenes may also be expressed throughout the entire plant tissue from a constitutive promoter. Combinations of tissue specific and constitutive promoters with the individual genes encoding the enzymes can also be varied to alter the amount and/or location of polymer production. It is also useful to be able to control the expression of these transgenes by using promoters that can be activated following the application of an agrochemical or other active ingredient to the crop in the field. Additional control of the expression of these genes encompassed by the methods described herein include the use of recombinase technologies for targeted insertion of the transgenes into specific chromosomal sites in the plant chromosome or to regulate the expression of the transgenes.

The methods described herein involve a plant seed having a genome including (a) a promoter operably linked to a first DNA sequence and a 3'-untranslated region, wherein the first DNA sequence encodes a fatty acid oxidation polypeptide and optionally (b) a promoter operably linked to a second DNA sequence and a 3'-untranslated region, wherein the second DNA sequence encodes a fatty acid oxidation polypeptide. Expression of the two transgenes provides the plant with a functional fatty acid 1-oxidation system having at least β-ketothiolase, dehydrogenase and hydratase activities in the cytoplasm or plastids other than peroxisomes or glyoxisomes. The first and/or second DNA sequence may be isolated from bacteria, yeast, fungi, algae, plants, or animals. It is preferable that at least one of the DNA sequences encodes a polypeptide with at least two, and preferably three, enzyme activities.

Transformation Vectors

DNA constructs useful in the methods described herein include transformation vectors capable of introducing transgenes into plants. Several plant transformation vector options are available, including those described in "Gene Transfer to Plants" (Potrykus, et al., eds.) Springer-Verlag Berlin Heidelberg New York (1995); "Transgenic Plants: A Production System for Industrial and Pharmaceutical Proteins" (Owen, et al., eds.) John Wiley & Sons Ltd. England (1996); and "Methods in Plant Molecular Biology: A Laboratory Course Manual" (Maliga, et al. eds.) Cold Spring Laboratory Press, New York (1995), which are incorporated herein by reference. Plant transformation vectors generally include one or more coding sequences of interest under the transcriptional control of 5' and 3' regulatory sequences, including a promoter, a transcription termination and/or polyadenylation signal, and a selectable or screenable marker gene. The usual requirements for 5' regulatory sequences include a promoter, a transcription termination and/or a polyadenylation signal. For the expression of two or more polypeptides from a single transcript, additional RNA processing signals and ribozyme sequences can be engineered into the construct (U.S. Pat. No. 5,519,164). This approach has the advantage of locating multiple transgenes in a single locus, which is advantageous in subsequent plant breeding efforts. An additional approach is to use a vector to specifically transform the plant plastid chromosome by homologous recombination (U.S. Pat. No. 5,545,818), in which case it is possible to take advantage of the prokaryotic nature of the plastid genome and insert a number of transgenes as an operon.

Promoters

A large number of plant promoters are known and result in either constitutive, or environmentally or developmentally regulated expression of the gene of interest. Plant promoters can be selected to control the expression of the transgene in different plant tissues or organelles for all of which methods are known to those skilled in the art (Gasser & Fraley, Science 244:1293–99 (1989)). The 5' end of the transgene may be engineered to include sequences encoding plastid or other subcellular organelle targeting peptides linked in-frame with the transgene. Suitable constitutive plant promoters include the cauliflower mosaic virus 35S promoter (CaMV) and enhanced CaMV promoters (Odell et. al., Nature, 313: 810 (1985)), actin promoter (McElroy et al., Plant Cell 2:163–71 (1990)), AdhI promoter (Fromm et. al., Bio/Technology 8:833–39 (1990); Kyozuka et al., Mol. Gen. Genet. 228:40–48 (1991)), ubiquitin promoters, the Figwort mosaic virus promoter, mannopine synthase promoter, nopaline synthase promoter and octopine synthase promoter. Useful regulatable promoter systems include spinach nitrate-inducible promoter, heat shock promoters, small subunit of ribulose biphosphate carboxylase promoters and chemically inducible promoters (U.S. Pat. No. 5,364,780 to Hershey et al.).

In a preferred embodiment of the methods described herein, the transgenes are expressed only in the developing seeds. Promoters suitable for this purpose include the napin gene promoter (U.S. Pat. Nos. 5,420,034 and 5,608,152), the acetyl-CoA carboxylase promoter (U.S. Pat. Nos. 5,420,034 and 5,608,152), 2S albumin promoter, seed storage protein promoter, phaseolin promoter (Slightom et. al., Proc. Natl. Acad. Sci. USA 80:1897–1901 (1983)), oleosin promoter (Plant et. al., Plant Mol. Biol. 25:193–205 (1994); Rowley et al., Biochim. Biophys. Acta. 1345:1–4 (1997); U.S. Pat. No. 5,650,554; and PCT WO 93/20216), zein promoter, glutelin promoter, starch synthase promoter, and starch branching enzyme promoter.

The transformation of suitable agronomic plant hosts using these vectors can be accomplished with a variety of methods and plant tissues. Representative plants useful in the methods disclosed herein include the Brassica family including napus, rappa, sp. carinata and juncea; maize; soybean; cottonseed; sunflower; palm; coconut; safflower; peanut; mustards including Sinapis alba; and flax. Crops harvested as biomass, such as silage corn, alfalfa, or tobacco, also are useful with the methods disclosed herein. Representative tissues for transformation using these vectors include protoplasts, cells, callus tissue, leaf discs, pollen, and meristems. Representative transformation procedures include Agrobacterium-mediated transformation, biolistics, microinjection, electroporation, polyethylene glycol-mediated protoplast transformation, liposome-mediated transformation, and silicon fiber-mediated transformation (U.S. Pat. No. 5,464,765; "Gene Transfer to Plants" (Potrykus, et al., eds.) Springer-Verlag Berlin Heidelberg New York (1995); "Transgenic Plants: A Production System for Industrial and Pharmaceutical Proteins" (Owen, et al., eds.) John Wiley & Sons Ltd. England (1996); and "Methods in Plant Molecular Biology: A Laboratory Course Manual" (Maliga, et al. eds.) Cold Spring Laboratory Press, New York (1995)).

II. Methods for Making and Screening for Transgenic Plants

In order to generate transgenic plants using the constructs described herein, the following procedures can be used to obtain a transformed plant expressing the transgenes subsequent to transformation: select the plant cells that have been transformed on a selective medium; regenerate the plant cells that have been transformed to produce differentiated plants; select transformed plants expressing the transgene at such that the level of desired polypeptide is obtained in the desired tissue and cellular location.

For the specific crops useful for practicing the described methods, transformation procedures have been established, as described for example, in "Gene Transfer to Plants" (Potrykus, et al., eds.) Springer-Verlag Berlin Heidelberg New York (1995); "Transgenic Plants: A Production System for Industrial and Pharmaceutical Proteins" (Owen, et al., eds.) John Wiley & Sons Ltd. England (1996); and "Methods in Plant Molecular Biology: A Laboratory Course Manual" (Maliga, et al. eds.) Cold Spring Laboratory Press, New York (1995).

Brassica napus can be transformed as described, for example, in U.S. Pat. Nos. 5,188,958 and 5,463,174. Other Brassica such as rappa, carinata and juncea as well as Sinapis alba can be transformed as described by Moloney et. al., Plant Cell Reports 8:238–42 (1989). Soybean can be transformed by a number of reported procedures (U.S. Pat. Nos. 5,015,580; 5,015,944; 5,024,944; 5,322,783; 5,416,011; and 5,169,770). Several transformation procedures have been reported for the production of transgenic maize plants including pollen transformation (U.S. Pat. No. 5,629,183), silicon fiber-mediated transformation (U.S. Pat. No. 5,464,765), electroporation of protoplasts (U.S. Pat. Nos. 5,231,019; 5,472,869; and 5,384,253) gene gun, (U.S. Pat. Nos. 5,538,877 and 5,538,880 and Agrobacterium-mediated transformation (EP 0 604 662 A1; PCT WO 94/00977). The Agrobacterium-mediated procedure is particularly preferred, since single integration events of the transgene constructs are more readily obtained using this procedure, which greatly facilitates subsequent plant breeding. Cotton can be transformed by particle bombardment (U.S. Pat. Nos. 5,004,863 and 5,159,135). Sunflower can be transformed using a combination of particle bombardment and Agrobacterium infection (EP 0 486 233 A2; U.S. Pat. No. 5,030,572). Flax can be transformed by either particle bombardment or Agrobacterium-mediated transformation. Recombinase technologies include the cre-lox, FLP/FRT, and Gin systems. Methods for utilizing these technologies are described for example in U.S. Pat. No. 5,527,695 to Hodges et al.; Dale & Ow, Proc. Natl. Acad. Sci. USA 8: 10558–62 (1991); Medberry et. al., Nucleic Acids Res. 23:485–90 (1995).

Selectable Marker Genes

Selectable marker genes useful in practicing the methods described herein include the neomycin phosphotransferase gene nptII (U.S. Pat. Nos. 5,034,322 and 5,530,196), hygromycin resistance gene (U.S. Pat. No. 5,668,298), bar gene encoding resistance to phosphinothricin (U.S. Pat. No. 5,276,268). EP 0 530 129 A1 describes a positive selection system which enables the transformed plants to outgrow the non-transformed lines by expressing a transgene encoding an enzyme that activates an inactive compound added to the growth media. Screenable marker genes useful in the methods herein include the β-glucuronidase gene (Jefferson et. al., EMBO J. 6:3901–07 (1987); U.S. Pat. No. 5,268,463) and native or modified green fluorescent protein gene (Cubitt et. al., Trends Biochem Sci. 20:448–55 (1995); Pang et. al., Plant Physiol. 112:893–900 (1996)). Some of these markers have the added advantage of introducing a trait, such as herbicide resistance, into the plant of interest, thereby providing an additional agronomic value on the input side.

In a preferred embodiment of the methods described herein, more than one gene product is expressed in the plant. This expression can be achieved via a number of different methods, including (1) introducing the encoding DNAs in a single transformation event where all necessary DNAs are on a single vector; (2) introducing the encoding DNAs in a co-transformation event where all necessary DNAs are on separate vectors but introduced into plant cells simultaneously; (3) introducing the encoding DNAs by independent transformation events successively into the plant cells i.e. transformation of transgenic plant cells expressing one or more of the encoding DNAs with additional DNA constructs; and (4) transformation of each of the required DNA constructs by separate transformation events, obtaining transgenic plants expressing the individual proteins and using traditional plant breeding methods to incorporate the entire pathway into a single plant.

III. β-Oxidation Enzyme Pathways

Production of PHAs in the cytosol of plants requires the cytosolic localization of enzymes that are able to produce R-3-hydroxyacyl CoA thioesters as substrates for PHA synthases. Both eukaryotes and prokaryotes possess a β-oxidation pathway for fatty acid degradation that consists of a series of enzymes that convert fatty acyl CoA thioesters to acetyl CoA. While these pathways proceed via intermediate 3-hydroxyacyl CoA, the stereochemistry of this intermediate varies among organisms. For example, the β-oxidation pathways of bacteria and the peroxisomal pathway of higher eukaryotes degrade fatty acids to acetyl CoA via S-3-hydroxyacyl CoA (Schultz, "Oxidation of Fatty Acids" in Biochemistry of Lipids, Lipoproteins and Membranes (Vance et al., eds.) pp. 101–06 (Elsevier, Amsterdam 1991)). In Escherichia coli, an epimerase activity encoded by the β-oxidation multifunctional enzyme complex is capable of converting S-3-hydroxyacyl CoA to R-3-hydroxyacyl CoA. Yeast possesses a peroxisomal localized fatty acid degradation pathway that proceeds via intermediate R-3-hydroxyacyl CoA (Hiltunen, et al. J. Biol. Chem. 267: 6646–53 (1992); Filppula, et al. J. Biol. Chem. 270:27453–57 (1995)), such that no epimerase activity is required to produce PHAs.

Plants, like other higher eukaryotes, possesses a β-oxidation pathway for fatty acid degradation localized subcellularly in the peroxisomes (Gerhardt, "Catabolism of Fatty Acids [(α and β Oxidation]" in Lipid Metabolism in Plants (Moore, Jr., ed.) pp. 527–65 (CRC Press, Boca Raton, Fla. 1993)). Production of PHAs in the cytosol of plants therefore necessitates the cytosolic expression of a β-oxidation pathway, for conversion of fatty acids to R-3-hydroxyacyl CoA thioesters of the correct chain length, as well as cytosolic expression of an appropriate PHA synthase, to polymerize R-3-hydroxyacyl CoA to polymer.

Fatty acids are synthesized as saturated acyl-ACP thioesters in the plastids of plants (Hartwood, "Plant Lipid Metabolism" in Plant Biochemistry (Dey et al., eds.) pp. 237–72 (Academic Press, San Diego 1997)). Prior to export from the plastid into the cytosol, the majority of fatty acids are desaturated via a Δ9 desaturase. The pool of newly synthesized fatty acids in most oilseed crops consists predominantly of oleic acid (cis 9-octadecenoic acid), stearic acid (octadecanoic acid), and palmitic acid (hexadecanoic acid). However, some plants, such as coconut and palm kernel, synthesize shorter chain fatty acids (C8–14). The fatty acid is released from ACP via a thioesterase and subsequently converted to an acyl-CoA thioester via an acyl CoA synthetase located in the plastid membrane (Andrews, et al., "Fatty acid and lipid biosynthesis and degradation" in Plant Physiology, Biochemistry, and Molecular Biology (Dennis et al., eds.) pp. 345–46 (Longman Scientific &

Technical, Essex, England 1990); Harwood, "Plant Lipid Metabolism" in *Plant Biochemistry* (Dey et al., eds) p. 246 (Academic Press, San Diego 1997)).

The cytosolic conversion of the pool of newly synthesized acyl CoA thioesters via fatty acid degradation pathways and the conversion of intermediates from these series of reactions to R-3-hydroxyacyl-CoA substrates for PHA synthases can be achieved via the enzyme reactions outlined in FIG. 1. The PHA synthase substrates are C4–C16 R-3-hydroxyacyl CoAs. For saturated fatty acyl CoAs, conversion to R-3-hydroxyacyl CoA thioesters using fatty acids degradation pathways necessitates the following sequence of reactions: conversion of the acyl CoA thioester to trans-2-enoyl-CoA (reaction 1), hydration of trans-2-enoyl-CoA to R-3-hyddroxy acyl CoA (reaction 2a, e.g. yeast system operates through this route and the *Aeromonas caviae* D-specific hydratase yields C4–C7 R-3-hydroxyacyl-CoAs), hydration of trans-2-enoyl-CoA to S-3-hydroxy acyl CoA (reaction 2b), and epimerization of S-3-hydroxyacyl CoA to R-3-hydroxyacyl CoA (reaction 5, e.g. cucumber tetrafunctional protein, bacterial systems). If 3-hydroxyacyl CoA is not polymerized by PHA synthase forming PHA, it can proceed through the remainder of the β-oxidation pathway as follows: oxidation of 3-hydroxyacyl CoA to form β-keto acyl CoA (reaction 3) followed by thiolysis in the presence of CoA to yield acetyl CoA and a saturated acyl CoA thioester shorter by two carbon units (reaction 4). The acyl CoA thioester produced in reaction 4 is free to re-enter the β-oxidation pathway at reaction 1 and the acetyl-CoA produced can be converted to R-3-hydroxyacyl CoA by the action of β-ketothiolase (reaction 7) and NADH or NADPH acetoacetyl-CoA reductase (reaction 6). This latter route is useful for producing R-3-hydroxybutyryl-CoA, R-3-hydroxyvaleryl-CoA and R-3-hydroxyhexanoyl-CoA. The R-3-hydroxyacids of four to sixteen carbon atoms produced by this series of enzymatic reactions can be polymerized by PHA synthases expressed from a transgene, or transgenes in the case of the two subunit synthase enzymes, into PHA polymers.

For Δ9 unsaturated fatty acyl CoAs, a variation of the reaction sequences described is required. Three cycles of β-oxidation, as detailed in FIG. 1, will remove six carbon units yielding an unsaturated acyl CoA thioester with a cis double bond at position 3. Conversion of the cis double bond at position 3 to a trans double bond at position 2, catalyzed by $\Delta^3$-cis-$\Delta^2$-trans-enoyl CoA isomerase will allow the β-oxidation reaction sequences outlined in FIG. 1 to proceed. This enzyme activity is present on the microbial β-oxidation complexes and the plant tetrafunctional protein, but not on the yeast fox1.

Acyl CoA thioesters also can be degraded to a β-keto acyl CoA and converted to R-3-hydroxyacyl CoA via a NADH or NADPH dependent reductase (reaction 6).

Multifunctional enzymes that encode S-specific hydratase, S-specific dehydrogenase, β-ketothiolase, epimerase and $\Delta^3$-cis-$\Delta^2$-trans-enoyl CoA isomerase activities have been found in bacteria such as *Escherichia coli* (Spratt, et al., *J. Bacteriol.* 158:535–42 (1984)) and *Pseudomonas fragi* (Immure, et al., *J. Biochem.* 17: 184–89 (1990)). The multifunctional enzyme complexes consist of two copies of each of two subunits such that catalytically active protein forms a heterotetramer. The hydratase, dehydrogenase, epimerase, and $\Delta^3$-cis-$\Delta^2$-trans-enoyl CoA isomerase activities are located on one subunit, whereas the thiolase is located on another subunit. The genes encoding the enzymes from organisms such as *E. coli* (Spratt, et al., *J. Bacteriol.* 158:535–42 (1984); DiRusso, *J. Bacteriol.* 172:6459–68 (1990)) and *P. fragi* (Sato, et al., *J. Biochem.* 111:8–15 (1992)) have been isolated and sequenced and are suitable for practicing the methods described herein. Furthermore, the *E. coli* enzyme system has been subjected to site-directed mutagenesis analysis to identify amino acid residues critical to the individual enzyme activities (He & Yang, *Biochemistry* 35:9625–30 (1996); Yang et. al., *Biochemistry* 34:6641–47 (1995); He & Yang, *Biochemistry* 36:11044–49 (1997); He et. al., *Biochemistry* 36:261–68 (1997); Yang & Elzinga, *J. Biol. Chem.* 268:6588–92 (1993)). These mutant genes also could be used in some embodiments of the methods described herein.

Mammals, such as rat, possess a trifunctional β-oxidation enzyme in their peroxisomes that contains hydratase, dehydrogenase, and $\Delta^3$-cis-$\Delta^2$-trans-enoyl CoA isomerase activities. The trifunctional enzyme from rat liver has been isolated and has been found to be monomeric with a molecular weight of 78 kDa (Palosaari, et al., *J. Biol. Chem.* 265:2446–49 (1990)). Unlike the bacterial system, thiolase activity is not part of the multienzyme protein (Schultz, "Oxidation of Fatty Acids" in *Biochemistry of Lipids, Lipoproteins and Membranes* (Vance et al., eds) p. 95 (Elsevier, Amsterdam (1991)). Epimerization in rat occurs by the combined activities of two distinct hydratases, one which converts R-3-hydroxyacyl CoA to trans-2-enoyl CoA, and another which converts trans-2-enoyl CoA to S-3-hydroxyacyl CoA (Smeland, et al., *Biochemical and Biophysical Research Communications* 160:988–92 (1989)). Mammals also possess β-oxidation pathways in their mitochondria that degrade fatty acids to acetyl CoA via intermediate S-3-hydroxyacyl CoA (Schultz, "Oxidation of Fatty Acids" in *Biochemistry of Lipids, Lipoproteins and Membranes* (Vance et al., eds) p. 96 (Elsevier, Amsterdam (1991)). Genes encoding mitochondrial β-oxidation activities have been isolated from several animals including a Rat mitochondrial long chain acyl CoA hydratase/3-hydroxy acyl CoA dehydrogenase (GENBANK Accession # D16478) and a Rat mitochondrial thiolase (GENBANK Accession #s D13921, D00511).

Yeast possesses a multifunctional enzyme, Fox2, that differs from the β-oxidation complexes of bacteria and higher eukaryotes in that it proceeds via a R-3-hydroxyacyl CoA intermediate instead of S-3-hydroxyacyl CoA (Hiltunen, et al., *J. Biol. Chem.* 267:6646–53 (1992)). Fox2 possesses R-specific hydratase and R-specific dehydrogenase enzyme activities. This enzyme does not possess the $\Delta^3$-cis-$\Delta^2$-trans-enoyl CoA isomerase activity needed for degradation of Δ9-cis-hydroxyacyl CoAs to form R-3-hydroxyacyl CoAs. The gene encoding fox2 from yeast has been isolated and sequenced and encodes a 900 amino acid protein. The DNA sequence of the structural gene and amino acid sequence of the encoded polypeptide is shown in SEQ ID NO:1 and SEQ ID NO:2.

Plants have a tetrafunctional protein similar to the yeast Fox2, but also encoding a $\Delta^3$-cis-$\Delta^2$-trans-enoyl CoA isomerase activity (Muller et., al., *J. Biol. Chem.* 269:20475–81 (1994)). The DNA sequence of the cDNA and amino acid sequence of the encoded polypeptide is shown in SEQ ID NO:3 and SEQ ID NO:4.

IV. Targeting of Enzymes to the Cytoplasm of Oil Seed Crops

Engineering PHA production in the cytoplasm of plants requires directing the expression of β-oxidation to the cytosol of the plant. No targeting signals are present in the bacterial systems, such as faoAB. In fungi, yeast, plants, and mammals, β-oxidation occurs in subcellular organelles. Typically, the genes are expressed from the nuclear chromosome, and the polypeptides synthesized in the cytoplasm are directed to these organelles by the presence of specific amino acid sequences. To practice the methods described herein using genes isolated from eukaryotic sources, e.g., fatty acid oxidation enzymes from eukaryotic sources, such as yeast, fungi, plants, and mammals, the removal or modification of subcellular targeting signals is required to direct the enzymes to the cytosol. It may be useful to add signals for directing proteins to the endoplasmic reticulum. Peptides useful in this process are well known in the art. The general approach is to modify the transgene by inserting a DNA sequence specifying an ER targeting peptide sequence to form a chimeric gene.

Eukaryotic acyl CoA dehydrogenases, as well as other mitrochondrial proteins, are targeted to the mitochondria via leader peptides on the N-terminus of the protein that are usually 20–60 amino acids long (Horwich, *Current Opinion in Cell Biology*, 2:625–33 (1990)). Despite the lack of an obvious consensus sequence for mitochondrial import leader peptides, mutagenesis of key residues in the leader sequence have been demonstrated to prevent the import of the mitochrondrial protein. For example, the import of *Saccharomyces cerevisiae* F1-ATPase was prevented by mutagenesis of its leader sequence, resulting in the accumulation of the modified precursor protein in the cytoplasm (Bedwell, et al., *Mol. Cell Biol.* 9:1014–25 (1989)).

Three eukaryotic peroxisomal targeting signals have been reported (Gould, et al., *J. Cell Biol.* 108:1657–64 (1989); Brickner, et al., *J. Plant Physiol.*, 113:1213–21 (1997)). The tripeptide targeting signal S/A/C-K/H/R-L occurs at the C-terminal end of many peroxisomal proteins (Gould, et al., *J. Cell Biol.* 108:1657–64 (1989)). Mutagenesis of this sequence has been shown to prevent import of proteins into peroxisomes. Some peroxisomal proteins do not contain the tripeptide at the C-terminal end of the protein. For these proteins, it has been suggested that targeting occurs via the tripeptide in an internal position within the protein sequence (Gould, et al., *J. Cell Biol.* 108:1657–64 (1989)) or via an unknown, unrelated sequence (Brickner, et al., *J. Plant Physiol.* 113:1213–21 (1997)). The results of in vitro peroxisomal targeting experiments with fragments of acyl CoA oxidase from *Candida tropicalis* appear to support the latter theory and suggest that there are two separate targeting signals within the internal amino acid sequence of the polypeptide (Small, et al., *The EMBO Journal* 7:1167–73 (1988)). In the aforementioned study, the targeting signals were localized to two regions of 118 amino acids in length, and neither of regions was found to contain the targeting signal S/A/C-K/H/R-L. A small number of peroxisomal proteins appear to contain an amino terminal leader sequence for import into peroxisomes (Brickner, et al., *J. Plant Physiol.* 113:1213–21 (1997)). These targeting signals can be deleted or altered by site directed mutagenesis.

V. Cultivation and Harvesting of Transgenic Plant

The transgenic plants can be grown using standard cultivation techniques. The plant or plant part also can be harvested using standard equipment and methods. The PHAs can be recovered from the plant or plant part using known techniques such as solvent extraction in conjunction with traditional seed processing technologies, as described in PCT WO 97/15681, or can be used directly, for example, as animal feed, where it is unnecessary to extract the PHA from the plant biomass.

Several lines which did not produce seed, produced much higher levels of biomass. This phenotype therefore may be useful as a means to increase the amount of green biomass produced per acre for silage, forage, or other biomass crops. End uses include the more cost effective production of forage crops for animal feed or as energy crops for electric power generation. Other uses include increasing biomass levels in crops, such as alfalfa or tobacco, for subsequent recovery of industrial products, such as PHAs by extraction.

The compositions and methods of preparation and use thereof described herein are further described by the following non-limiting examples.

EXAMPLE 1

Isolation and Characterization of the *Pseudomonas putida* fao AB Genes and Fao Enzyme All DNA manipulations, including PCR, DNA sequencing *E. coli* transformation, and plasmids purification, were performed using standard procedures, as described, for example, by Sambrook et. al., Molecular Cloning: A Laboratory Manual (Cold Spring Harbor Laboratory Press, New York (1989)). The genes encoding faoAB from *Pseudomonas putida* were isolated using a probe generated from *P. putida* genomic DNA by PCR (polymerase chain reaction) using primers 1 and 2 possessing homology to faoB from *Pseudomonas fragi* (Sato, et al., *J. Biochem.* 111:8–15 (1992)).

Primer 1:

5' gat ggg ccg ctc caa ggg tgg 3' (SEQ ID NO:5)

Primer 2:

5' caa ccc gaa ggt gcc gcc att 3' (SEQ ID NO:6)

A 1.1 kb DNA fragment was purified from the PCR reaction and used as a probe to screen a *P. putida* genomic library constructed in plasmid pBKCMV using the lambda ZAP expression system (Stratagene). Plasmid pMFX1 was selected from the positive clones and the DNA sequence of the insert containing the faoAB genes and flanking sequences determined. This is shown in SEQ ID NO:7. A fragment containing faoAB was subcloned with the native *P. putida* ribosome binding site intact into the expression vector pTRCN forming plasmid pMFX3 as follows. Plasmid pMFX1 was digested with BsrG I. The resulting protruding ends were filled in with Klenow. Digestion with Hind III yielded a 3.39 kb blunt ended/Hind III fragment encoding FaoAB. The expression vector pTRCN was digested with Sma I/Hind III and ligated with the faoAB fragment forming the 7.57 kb plasmid pMFX3.

Enzymes in the FaoAB multienzyme complex were assayed as follows. Hydratase activity was assayed by monitoring the conversion of NAD to NADH using the coupling enzyme L-β-hydroxyacyl CoA dehydrogenase as previously described, except that assays were run in the presence of CoA (Filppula, et al., *J. Biol. Chem.* 270:27453–57 (1995)). Severe product inhibition of the coupling enzyme was observed in the absence of CoA. The assay contained (1 mL final volume) 60 $\mu$M crotonyl CoA, 50 $\mu$M Tris-CI, pH 9, 50 $\mu$g bovine serum albumin per mL, 50 mM KCl, 1 mM NAD, 7 $\mu$g L-specific β-hydroxyacyl CoA dehydrogenase from porcine heart per mL, and 0.25 mM CoA. The assay was initiated with the addition of FaoAB to the assay mixture. A control assay was performed without substrate to determine the rate of consumption of NAD in the absence of the hydratase generated product, S-hydroxybutyryl CoA. One unit of activity is defined as the consumption of one $\mu$Mol of NAD per min ($\epsilon_{340}$=6220 $M^-cm^{-1}$).

Hydroxyacyl CoA dehydrogenase was assayed in the reverse direction with acetoacetyl CoA as the substrate by monitoring the conversion of NADH to NAD at 340 nm (Binstock, et al., *Methods in Enzymology*, 71:403 (1981)). The assay contained (1 mL final volume) 0.1 M $KH_2PO_4$, pH 7, 0.2 mg bovine serum albumin per mL, 0.1 mM NADH, and 33 μM acetoacetyl CoA. The assay was initiated with the addition of FaoAB to the assay mixture. When necessary, enzyme samples were diluted in 0.1 M $KH_2PO_4$, pH 7, containing 1 mg bovine serum albumin per mL. A control assay was performed without substrate acetoacetyl CoA to detect the rate of consumption of NADH in the crude due to enzymes other than hydroxyacyl CoA dehydrogenase. One unit of activity is defined as the consumption of one μMol of NADH per minute ($\epsilon_{340}$=6220 $M^{-1}cm^{-1}$).

HydroxyacylCoA dehydrogenase was assayed in the forward direction with crotonyl CoA as a substrate by monitoring the conversion of NAD to NADH at 340 nm (Binstock, et al., Methods in Enzymology, 71:403 (1981)). The assay mixture contained (1 mL final volume) 0.1 M $KH_2PO_4$, pH 8, 0.3 mg bovine serum albumin per mL, 2 mM β-mercaptoethanol, 0.25 mM CoA, 30 μM crotonyl CoA, and an aliquot of FaoAB. The reaction was preincubated for a couple of minutes to allow in situ formation of S-hydroxybutyryl CoA. The assay then was initiated by the addition of NAD (0.45 mM). A control assay was performed without substrate to detect the rate of consumption of NAD due to enzymes other than hydroxyacyl CoA dehydrogenase. One unit of activity is defined as the consumption of one pMol of NAD per minute ($\epsilon_{340}$=6220 $M^{-1}cm^{-1}$).

Thiolase activity was determined by monitoring the decrease in absorption at 304 nm due to consumption of substrate acetoacetyl CoA as previously described with some modifications (Palmer, et al., J. Biol. Chem. 266:1–7 (1991)). The assay contained (final volume 1 mL) 62.4 mM Tris-Cl, pH 8.1, 4.8 mM $MgCl_2$, 62.5 μM CoA, and 62.5 μM acetoacetyl CoA. The assay was initiated with the addition of FaoAB to the assay mixture. A control sample without enzyme was performed for each assay to detect the rate of substrate degradation of pH 8.1 in the absence of enzyme. One unit of activity is defined as the consumption of one μMol of substrate acetoacetyl CoA per minute ($\epsilon_{340}$=16900 $M^{-1}cm^{-1}$).

Epimerase activity was assayed as previously described (Binstock, et al., Methods in Enzymology, 71:403 (1981)) except that R-3-hydroxyacyl CoA thioesters were utilized instead of D,L-3-hydroxyacyl CoA mixtures. The assay contained (final volume 1 mL) 30 μM R-3-hydroxyacyl CoA, 150 mM $KH_2PO_4$ (pH 8), 0.3 mg/mL BSA, 0.5 mM NAD, 0.1 mM CoA, and 7 μg/mL L-specific β-hydroxyacyl CoA dehydrogenase from porcine heart. The assay was initiated with the addition of FaoAB.

For expression of FaoAB in DH5(α/pMFX3, cultures were grown in 2×TY medium at 30° C. 2×TY medium contains (per L) 16 g tryptone, 10 g yeast, and 5 g NaCl. A starter culture was grown overnight and used to inoculate (1% inoculum) fresh medium (100 mL in a 250 mL Erlenmeyer flask for small scale growths; 1.5 L in a 2.8 L flask for large scale growths). Cells were induced with 0.4 mM IPTG when the absorbance at 600 nm was in the range of 0.4 to 0.6. Cells were cultured an additional 4 h prior to harvest. Cells were lysed by sonication, and the insoluble matter was removed from the soluble proteins by centrifugation. Acyl CoA dehydrogenase activity was monitored in the reverse direction to ensure activity of the FaoA subunit (SEQ ID NO:3 1) and thiolase activity was assayed to determine activity of the Fao subunit. FaoAB in DH5α/pMFX3 contained dehydrogenase and thiolase activity values of 4.3 and 0.99 U/mg, respectively, which is significantly more than the 0.0074 and 0.0033 U/mg observed for dehydrogenase and thiolase, respectively, in control strain DH5α/pTRCN.

FaoAB was purified from DH5α/pMFX3 using a modified procedure previously described for the purification of FaoAB from Pseudomonas fragi (Imamura, et al., J. Biochem. 107:184–89 (1990)). Thiolase activity (assayed in the forward direction) and dehydrogenase activities (assayed in the reverse direction) were monitored throughout the purification. Three liters of DH5α/pMFX3 cells (2×1.5 L aliquots in 2.8 L Erlenmeyer flasks) were grown in 2×TY medium using the cell growth procedure previously described for preparing cells for enzyme activity analysis. Cells (15.8 g) were resuspended in 32 mL of 10 mM $KH_2PO_4$, pH 7, and lysed by sonication. Soluble proteins were removed from insoluble cells debris by centrifugation (18,000 RPM, 30 min., 4° C.). The soluble extract was made 50% in acetone and the precipitated protein was isolated by centrifugation and redissolved in 10 mM $KH_2PO_4$, pH 7. The sample was adjusted to 33% saturation with $(NH_4)_2SO_4$ and the soluble and insoluble proteins were separated by centrifugation. The resulting supernatant was adjusted to 56% saturation with $(NH_4)_2SO_4$ and the insoluble pellet was isolated by centrifugation and dissolved in 10 mM $KH_2PO_4$, pH 7. The sample was heated at 50° C. for 30 min. and the soluble proteins were isolated by centrifugation and dialyzed in a 6,000 to 8,000 molecular weight cut off membrane in 10 mM $KH_2PO_4$, pH 7 (2×3 L; 20 h). The sample was loaded on a Toyo Jozo DEAE FPLC column (3 cm×14 cm) that previously had been equilibrated in 10 mM $KH_2PO_4$, pH 7. The protein was eluted with a linear gradient (100 mL by 100 mL; 0 to 500 mM NaCl in 10 $KH_2PO_4$, pH 7) at a flow of 3 mL/min. FaoAB eluted between 300 and 325 mM NaCl. The sample was dialyzed in a 50,000 molecular weight cut off membrane in 10 mM $KH_2PO_4$, pH 7 (1×2 L; 15 h) prior to loading on a macro-prep hydroxylapatite 18/30 (Biorad) FPLC column (2 cm×15 cm) that previously had been equilibrated in 10 mM $KH_2PO_4$, pH 7. The protein was eluted with a linear gradient (250 mL by 250 mL; 10 to 500 mM $KH_2PO_4$, pH 7) at a flow rate of 3 mL/min. FaoAB eluted between 70 and 130 mM $KH_2PO_4$. The fractions containing activity were concentrated to 9 mL using a MILLFPORE™ 100,000 molecular weight cutoff concentrator. The buffer was exchanged 3 times with 10 mM $KH_2PO_4$, pH 7 containing 20% sucrose and frozen at −70° C. Enzyme activities of the hydroxylapatite purified fraction were assayed with a range of substrates. The results are shown in Table 1 below.

TABLE 1

Enzyme Substrates and Activities

| Enzyme | Substrate | Activity (U/mg) |
| --- | --- | --- |
| hydratase | crotonyl CoA | 8.8 |
| dehydrogenase (forward) | crotonyl CoA | 0.46 |
| dehydrogenase (reverse) | acetoacetyl CoA | 29 |
| thiolase | acetoacetyl CoA | 9.9 |
| epimerase | R-3-hydroxyoctanyl CoA | 0.022 |
| epimerase | R-3-hydroxyhexanyl CoA | 0.0029 |
| epimerase | R-3-hydroxybutyryl CoA | 0.000022 |

EXAMPLE 2

Production of Antibodies to the FaoAB and FaoAB Polypeptides

Following purification of the FaoAB protein as described in Example 1, a sample was separated by SDS-PAGE. The protein band corresponding to the FaoA (SEQ ID NO:31) and FaoB (SEQ ID NO:26) was excised and used to immunize New Zealand white rabbits with complete Freunds adjuvant. Boosts were performed using incomplete Freunds at three week intervals. Antibodies were recovered from serum by affinity chromatography on Protein A columns (Pharmacia) and tested against the antigen by Western blotting procedures. Control extracts of Brassica seeds were used to test for cross reactivity to plant proteins. No cross reactivity was detected.

EXAMPLE 3

Construction of Plasmids for Expression of the *Pseudomonas putido* fao AB Genes in Transgenic Oilseeds Construction of pSBS2024

Oligonucleotide primers GVR471

5'-CGGTACCCATTGTACTCCCAGTATCAT-3' (SEQ ID NO:8)

and GVR472

Figure 2:
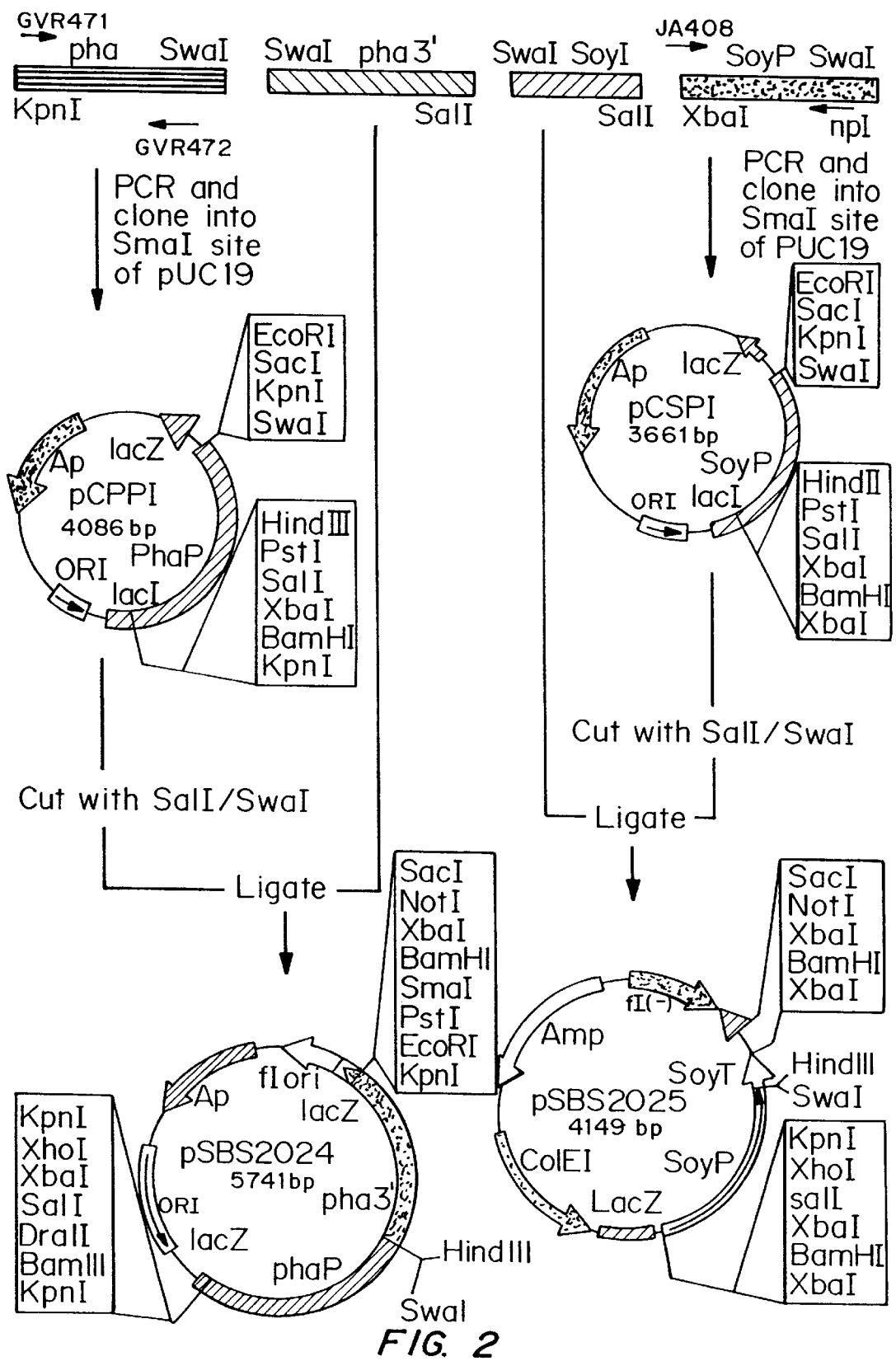
FIG. 2 is a schematic showing plasmid constructs pSBS2024 and pSBS2025.

5'-CATTTAAATAGTAGAGTATTGAATATG-3' (SEQ ID NO:9)

homologous to sequences flanking the 5' and 3' ends (underlined), respectively, of the bean phaseolin promoter (SEQ ID NO:10; Slightom et al., 1983) were designed with the addition of KpnI (in italics, nucleotides 1–7 in SEQ ID NO:8) and SwaI (in italics, nucleotides 1–9 in SEQ ID NO:9) at the 5' ends of GVR471 and GVR472, respectively. These restriction sites were incorporated to facilitate cloning. The primers were used to amplify a 1.4 kb phaseolin promoter, which was cloned at the SmaI site in pUC19 by blunt ended ligation. The designated plasmid, pCPPI (see FIG. 2) was cut with SalI and SwaI and ligated to a SalI/SwaI phaseolin terminator (SEQ ID NO:27). The bean phaseolin terminator sequence encompassing the polyadenylation signals was amplified using the following PCR primers:

GVR396:

5'-GATTTAAATGCAAGCTTAAATAAGTATGAACTAA AATGC-3' (SEQ ID NO:22)

and GVR397:

5'-CGGTACCTTAGTTGGTAGGGTGCTA-3' (SEQ ID NO.23)

and the 1.2 Kb fragment (SEQ ID NO:27) cloned into Sal1-Sal site of pCCP1 to obtain pSBS2024 (FIG. 2). The resulting plasmid which contains a unique HindIII site for cloning was called pSBS2024 (FIG. 2).

Construction of pSBS2025

A soybean oleosin promoter fragment (SEQ ID NO:11; Rowley et al., 1997) was simplified with primers that flank the DNA sequence.

Primer JA408

5' -TCTA GATACATCCATTTCTTAATATAATCCTCTTATTC-3' (SEQ ID NO:12)

contains sequences that are complementary to the 5' end (underlined).

Primer np1

5' -CA TTTAAA TGGTTAAGGTGAAGGTAGGGCT-3' (SEQ ID NO:13)

contains sequences homologous to the 3' end (underlined) of the promoter fragment. The restriction sites XbaI (in italics) and SwaI (in italics) were incorporated at the 5' end of JA408 and np1, respectively, to facilitate cloning. The primers were used to amplify a 975 bp promoter fragment, which then was cloned into SmaI site of pUC19 (see FIG. 2). The resulting plasmid, pCSPI, was cut with SalI and SwaI and ligated to the soybean terminator (SEQ ID NO:28). The soybean oleosin terminator was amplified by PCR using the following primers:

JA410:

5'-AAGCTTACGTGATGAGTATTAATGTGTTGTTATG-3' (SEQ ID NO:29) and

JA411:

5'-TCTAGACAATTCATCAAATACAAATCACATTGCC-3' (SEQ ID NO:30)

and the 225 bp fragment cloned into the SalI-SwaI site of pCSP1 to obtain plasmid pSBS2025 (FIG. 6). The designated plasmid, pSBS2025, carried a unique HindIII site for cloning (FIG. 2).

Construction of Promoter-coding Sequence Fusions

Two oligonucleotide primers were synthesized:

np2

5'AAGCTTAAAATGATTTACGAAGGTAAAGCC-3' (SEQ ID NO:14)

homologous to nucleotides 553 to 573 of the 5' flanking sequences, and np3

Figure 3A:
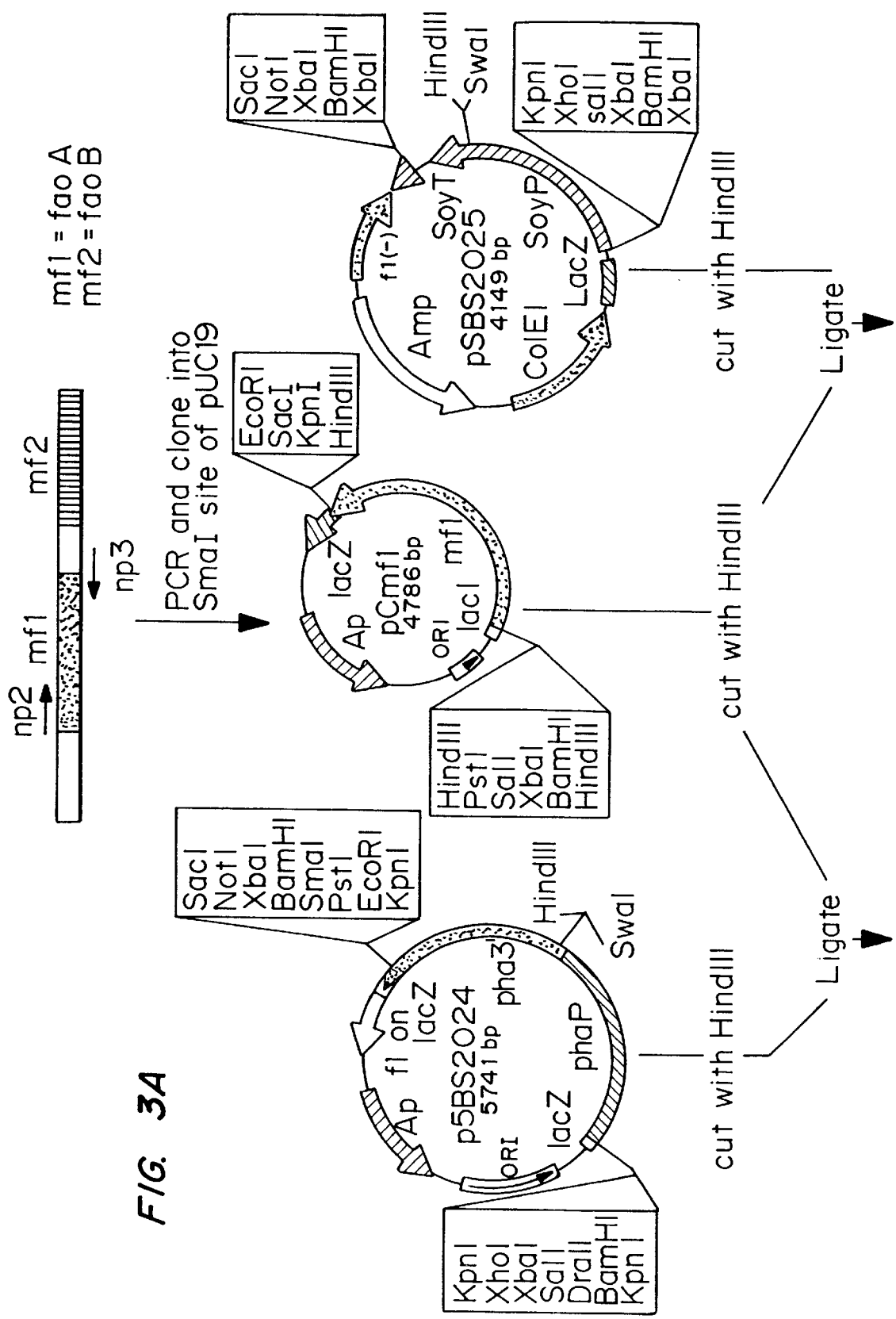
FIGS. 3A and 3B are schematics showing plasmid constructs pCGmf124 and pCGmf125.
Figure 3B:
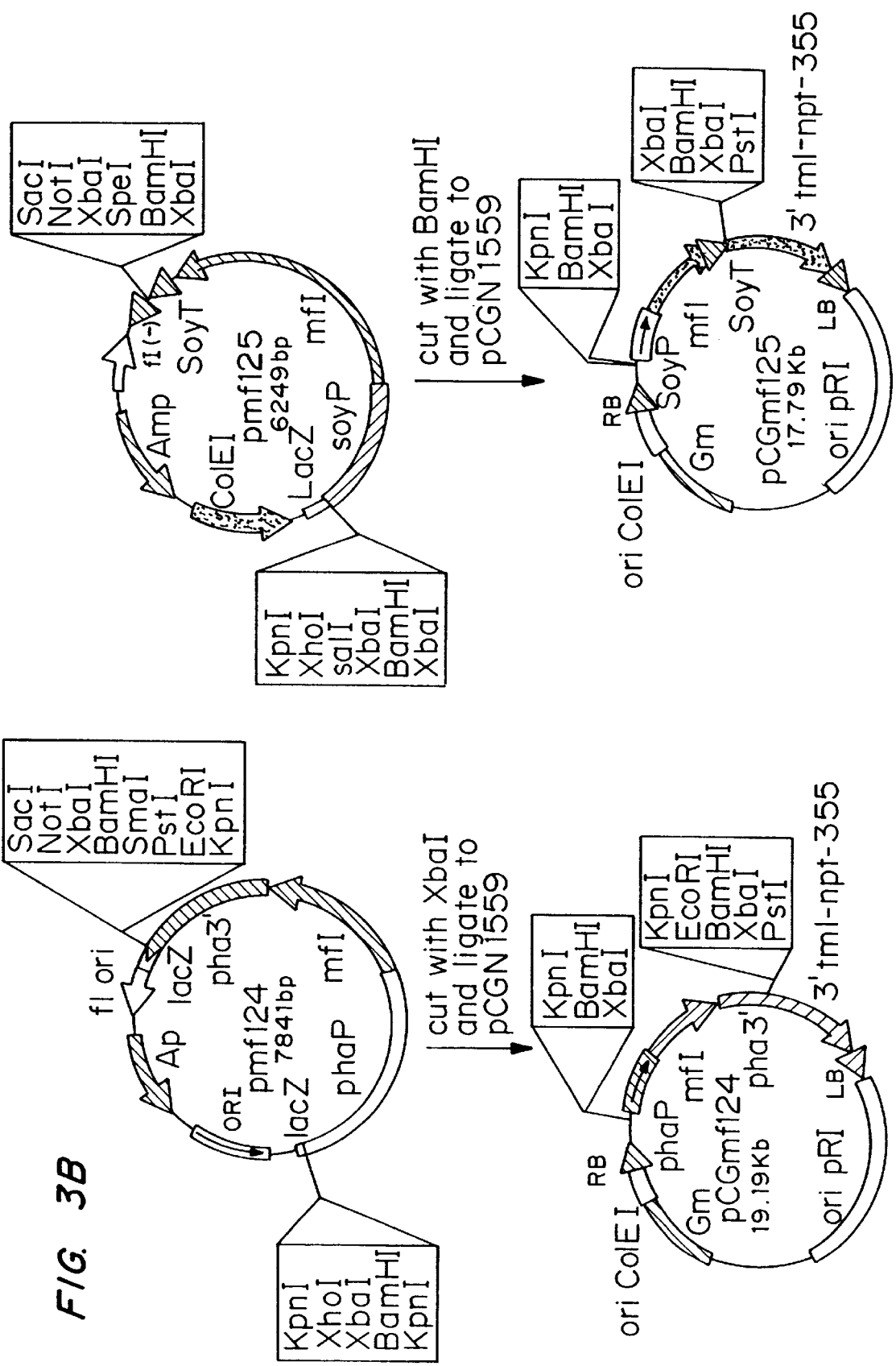
Figure 5A:
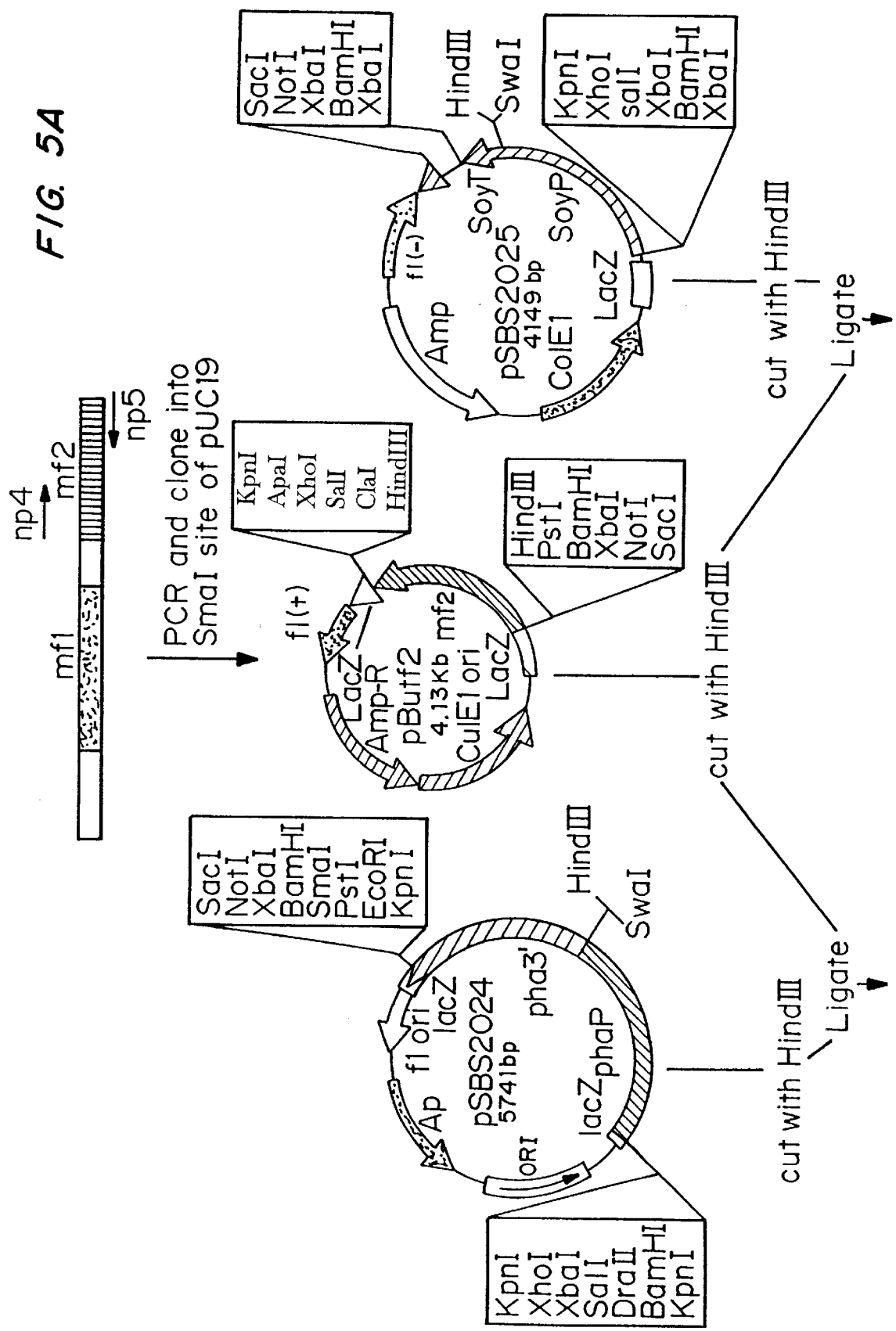
FIGS. 5A and 5B are schematics showing plasmid constructs pCGmf224 and pCGmf225.
Figure 5B:
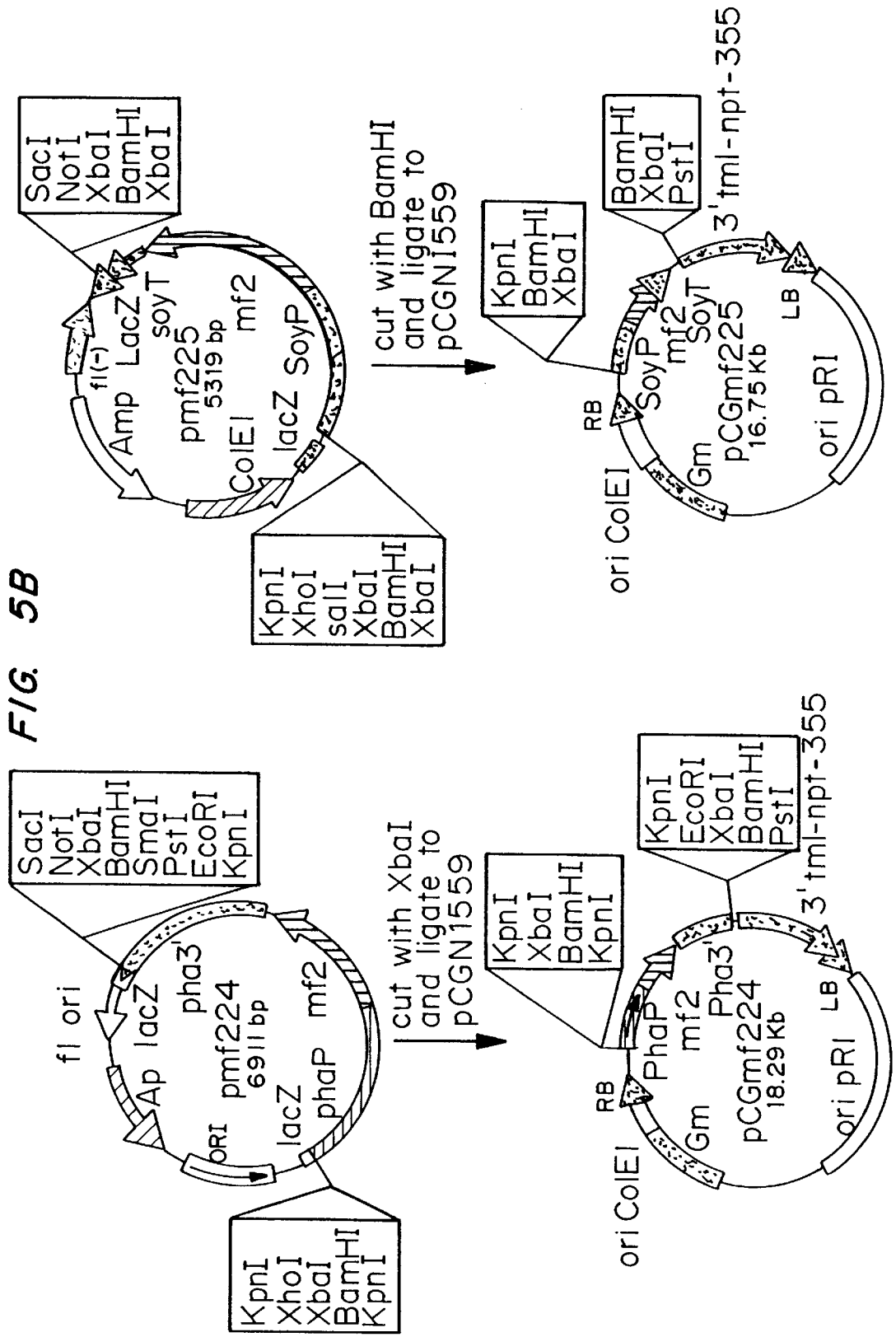

5' A TTGCTTFCAGTTGAAGCGCTG-3' (SEQ ID NO:15)

complementary to nucleotides 2700 to 2683 flanking the 3' end of mf1 (faoA, SEQ ID NO:24) of plasmid pmfx3. A HindIII (in italics) site was introduced at the 5' end of primers np2 and np3 to facilitate cloning. In addition, a 3 bp AAA sequence (bold) was incorporated to obtain a more favorable sequence surrounding the plant translational initiation codon. Primers np2 and np3 were used to amplify the fragment and cloned into SmaI site of pUC19. The resulting plasmid was called pCmfI (FIGS. 3A and 3B). Plasmid pBmf2 was constructed in a similar process (FIGS. 5A and 5B). In order to generate a HindIII (in italics) at 5' and 3' ends of the mf2 (faoB) gene (SEQ ID NO:25) for cloning, a second set of synthetic primers were designed.

Primers np4

5' -AAGCTTAAAATGAGCCTGAATCCAAGAGAC-3' (SEQ ID NO:16)

complementary to 5' (nucleotides 2732–2752 bp) and np5

5'AAGCTTTCAGACGCGTTCGAAGACAGTG -3' (SEQ ID NO:17)

homologous to 3' (nucleotides 3907–3886 bp) sequences of mf2 (faoB, SEQ ID NO:25) of plasmid pmfx3 were used in a PCR reaction to amplify the 1.17 kb DNA fragment. The resulting PCR product was cloned into the EcoRV site of pBluescript. The plasmid was referred to as pBmf2.

Both plasmids were individually cut with HindIII and their inserts cloned in plasmids pSBS2024 and pSBS2025, which had previously been linearized with the same restriction enzyme. As a result, the following plasmids were generated: pmf124 and pmf125 (FIGS. 3A and 3B) and pmf224 and pmf225 (FIGS. 5A and 5B) containing the Fao genes (mf1 and mf2) fused to either the phaseolin or soybean promoters. DNA sequence analysis confirmed the correct promoter-coding sequence-termination sequence fusions for pmf124, pmf125, pmf224, and pmf225.

EXAMPLE 4

Assembly of Promoter-coding Sequence Fusions into Plant Transformation Vectors

After obtaining plasmids pmf124, pmf125, pmf224, and pmf225, promoter-coding sequence fusions were independently cloned into the binary vectors, pCGN1559 (McBride and Summerfelt, 1990) containing the CaMV 35S promoter driving the expression of NPTII gene (conferring resistance to the antibiotic kanamycin) and pSBS2004 containing a parsley ubiquitin promoter driving the PPT gene, which confers resistance to the herbicide phosphinothricine. Binary vectors suitable for this purpose with a variety of selectable markers can be obtained from several sources.

The phaseolin-mf21 fusion cassette was released from the parent plasmid with XbaI and ligated with pCGN1559, which had been linearized with the same restriction enzyme.

The resulting plasmid was designated pCGmf124 (FIGS. 3A and 3B). Plasmid pCGmf125 containing the soybean-mf1 fusion was constructed in a similar way (FIGS. 3A and 3B), except that both pmf125 and pCGN1559 were cut with BamHI before ligation.

Construction of pmf1249 an pmf1254

Figure 4A:
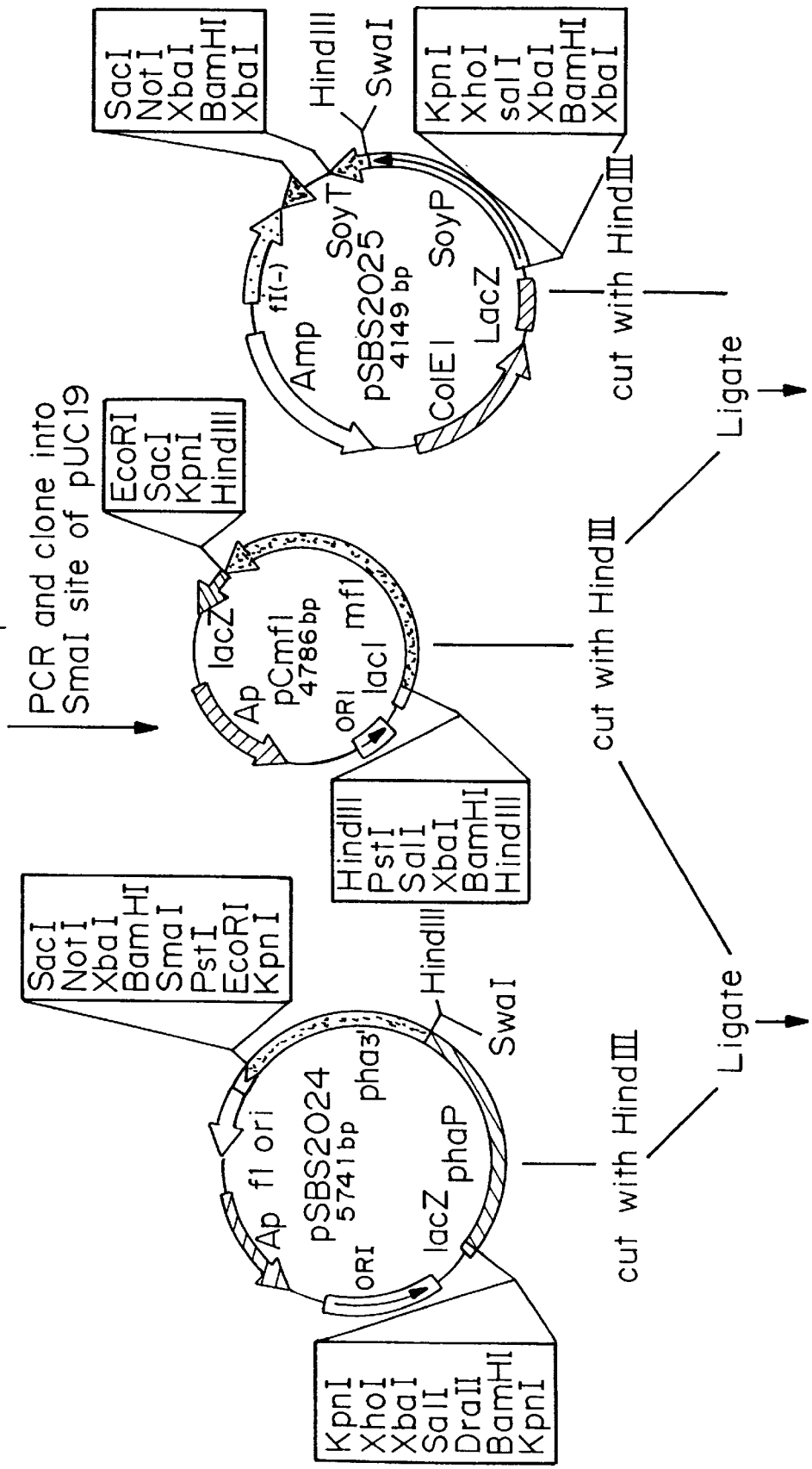
FIGS. 4A and 4B are schematics showing plasmid constructs pmf1249 and pmf1254.
Figure 4B:
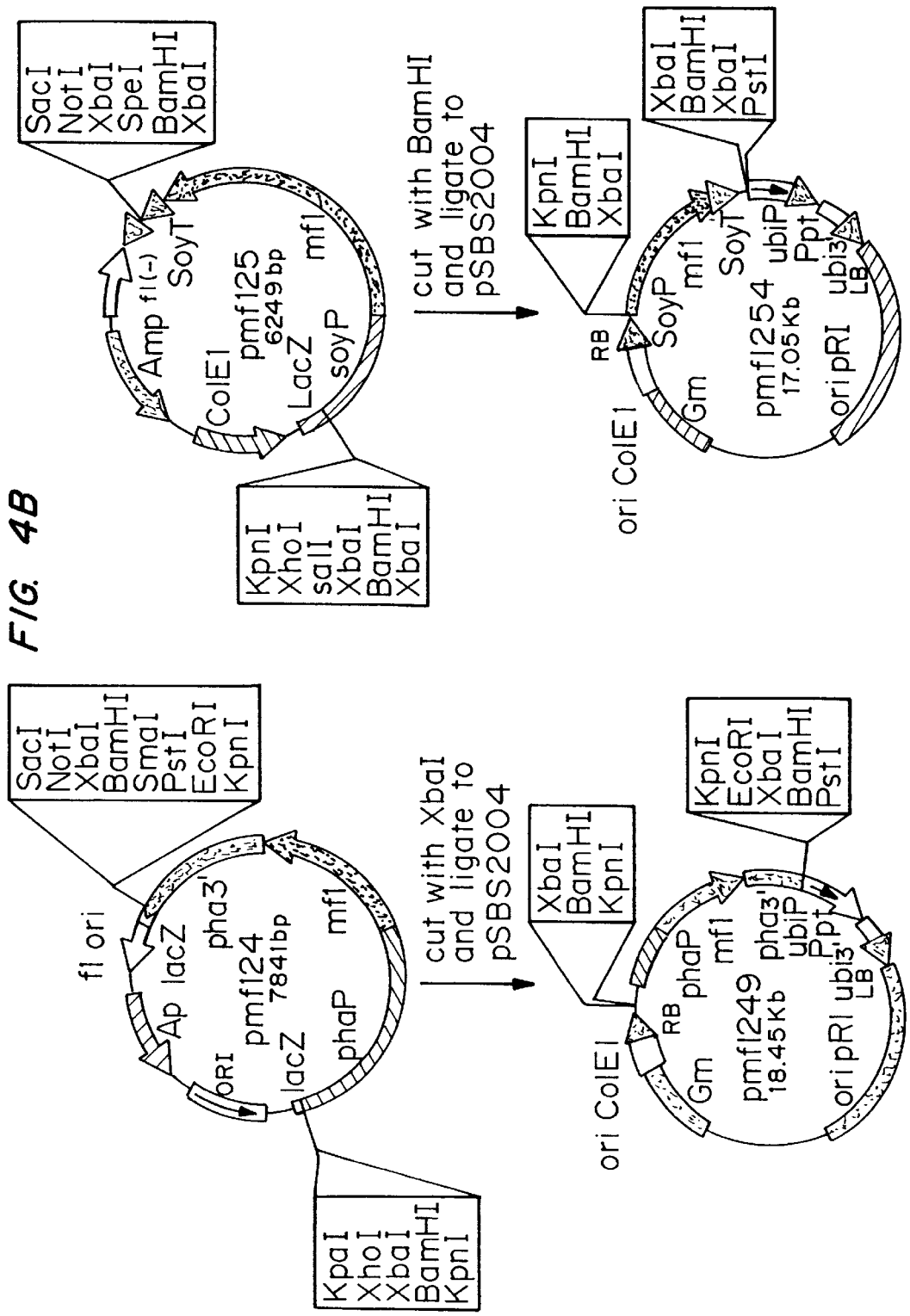

The plasmid pSBS2004 was linearized with BamHI fragment containing the soybean-mf1 fusion. This plasmid was designated pmf1254 (FIGS. 4A and 4B). Similarly, the XbaI phaseolin-mf1 fusion fragment was ligated to pSBS2004 which had been linearized with the same restriction enzyme. The resulting plasmid was designated pmf1249 (FIGS. 4A and 4B).

Construction of pCGmf224 and pCGmf225

The phaseolin-mf2 and soybean-mf2 fusions were constructed by excising the fusions from the vector by cutting with either BamHI or XbaI, and cloned into pCGN1559 which had been linearized with either restriction enzyme (FIGS. 5A and 5B).

Construction of pCGmf1P2S and pCGmf2P1S

Figure 6A:
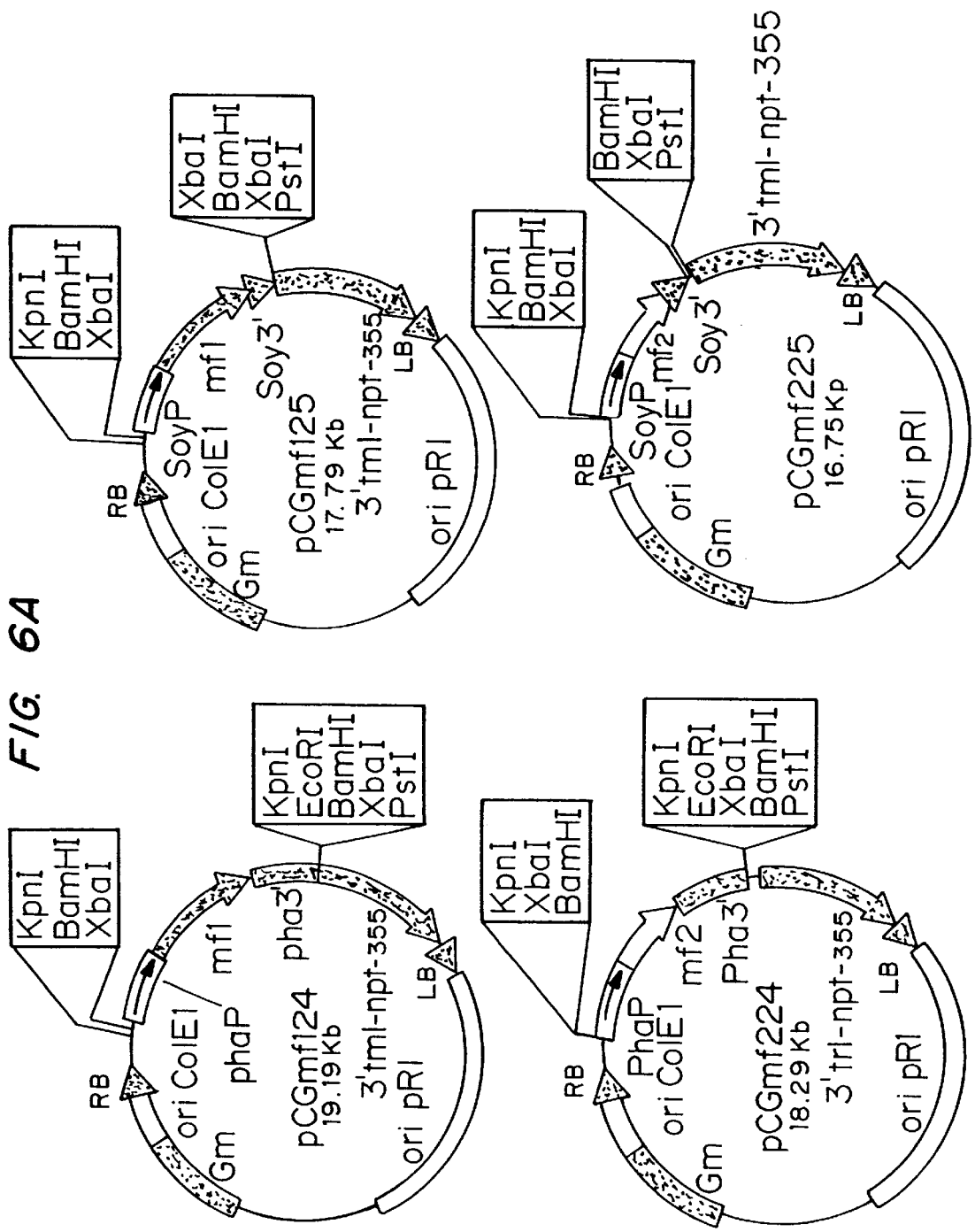
FIGS. 6A and 6B are schematics showing plasmid constructs pCGmf1P2S and pCGmf2P1S.
Figure 6B:
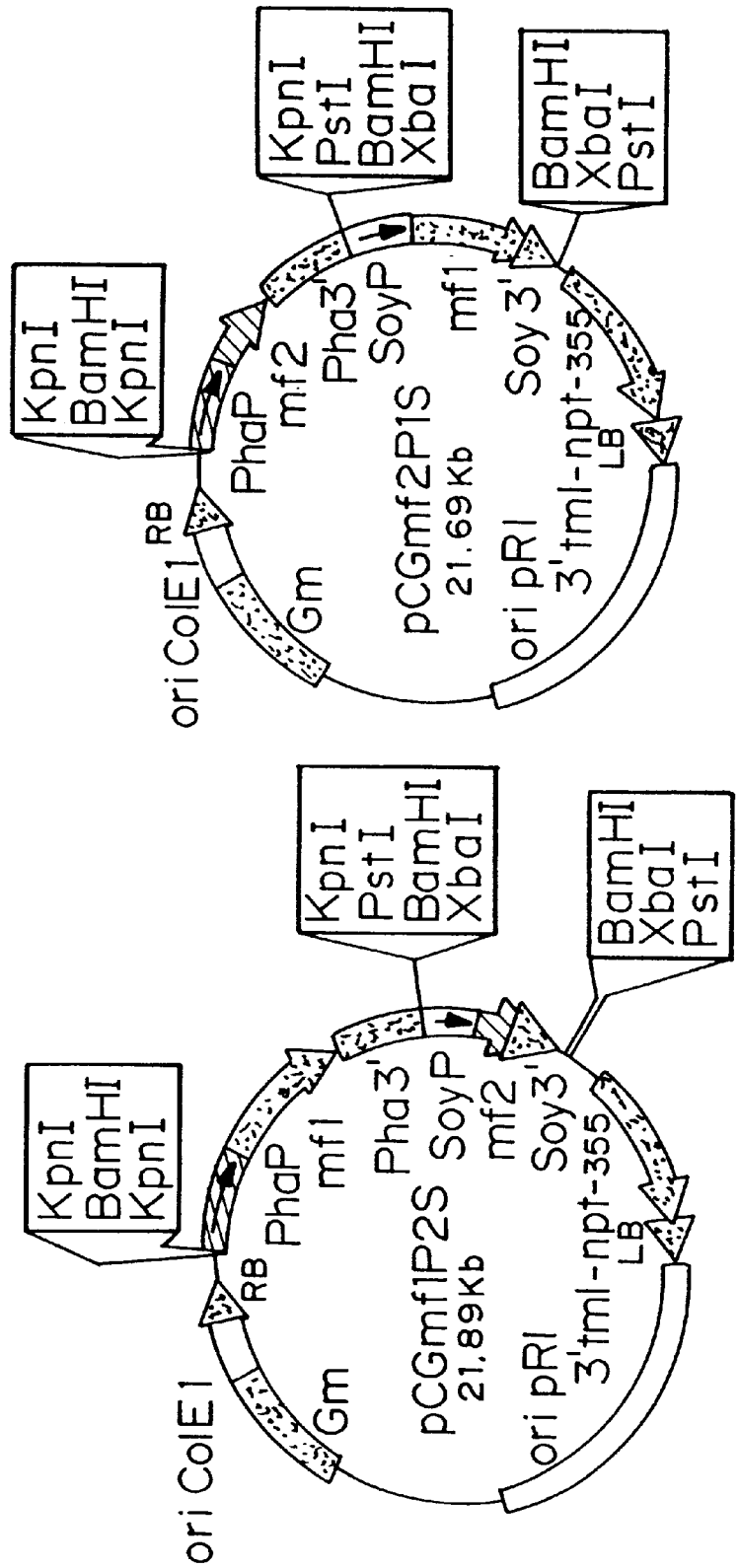

The two expression cassettes containing the promoter-coding sequence fusions were assembled on the same binary vector as follows: Plasmid pmf124 containing the phaseolin-mf1 fusion was cut with BamHI and cloned into the BamHI site of pCGN1559 to create pCGmfB124. This plasmid then was linearized with XbaI and ligated to the XbaI fragment of pmf225 containing the soybean-mf2 fusion. The final plasmid was designated pCGmf1P2S (FIGS. 6A and 6B). Plasmid pCGmf2P1S was assembled in similar manner. The phaseolin-mf2 fusion was released from pmf224 by cutting with BamHI and cloned at the BamHI site of pCGN1559. The resulting plasmid, pCGmfB224, was linearized with XbaI and ligated to the XbaI fragment of pmf125 containing the soybean-mf1 fusion (FIGS. 6A and 6B).

EXAMPLE 5

Transformation of Brassica

Brassica seeds were surface sterilized in 10% commercial bleach (Javex, Colgate-Palmolive) for 30 min. with gentle shaking. The seeds were washed three times in sterile distilled water. Seeds were placed in germination medium comprising Murashige-Skoog (MS) salts and vitamins, 3% (w/v) sucrose and 0.7% (w/v) phytagar, pH 5.8 at a density of 20 per plate and maintained at 24° C. and a 16 h light/8 h dark photoperiod at a light intensity of 60–80 $\mu Em^{-2}s^{-1}$ for four to five days.

Each of the constructs, pCGmf124, pCGmf125, pCGmf224, pCGmf1P2S, and pCGmf2P1S were introduced into *Agrobacterium tumefacians* strain EHA101 (Hood et al., *J. Bacteriol.* 168:1291–1301 (1986)) by electroporation. Prior to transformation of cotyledonary petioles, single colonies of strain EHA101 harboring each construct were grown in 5 ml of minimal medium supplemented with 100 mg kanamycin per liter and 100 mg gentamycin per liter for 48 hr at 28° C. One milliliter of bacterial suspension was pelletized by centrifugation for 1 min in a microfuge. The pellet was resuspended in 1 ml minimal medium.

For transformation, cotyledons were excised from 4 day old, or in some cases 5 day old, seedlings, so that they included approximately 2 mm of petiole at the base. Individual cotyledons with the cut surface of their petioles were immersed in diluted bacterial suspension for 1 s and immediately embedded to a depth of approximately 2 mm in co-cultivation medium, MS medium with 3% (w/v) sucrose and 0.7% phytagar and enriched with 20 $\mu$M benzyladenine. The inoculated cotyledons were plated at a density of 10 per plate and incubated under the same growth conditions for 48 h. After co-cultivation, the cotyledons then were transferred to regeneration medium comprising MS medium supplemented with 3% sucrose, 20 $\mu$M benzyladenine, 0.7% (w/v) phytagar, pH 5.8, 300 mg timentinin per liter, and 20 mg kanamycin sulfate per liter.

After two to three weeks, regenerant shoots obtained were cut and maintained on "shoot elongation" medium (MS medium containing, 3% sucrose, 300 mg timentin per liter, 0.7% (w/v) phytagar, 300 mg timentinin per liter, and 20 mg kanamycin sulfate per liter, pH 5.8) in Magenta jars. The elongated shoots were transferred to "rooting" medium comprising MS medium, 3% sucrose, 2 mg indole butyric acid per liter, 0.7% phytagar, and 500 mg carbenicillin per liter. After roots emerged, plantlets were transferred to potting mix (Redi Earth, W. R. Grace and Co.). The plants were maintained in a misting chamber (75% relative humidity) under the same growth conditions. Two to three weeks after growth, leaf samples were taken for neomycin phosphotransferase (NPTII) assays (Moloney et al., *Plant Cell Reports* 8:238–42 (1989)).

Seeds from the FaoA and FaoB transgenic lines can be analyzed for expression of the fatty acid oxidation polypeptides by western blotting using the anti-FaoA and anti-FaoB antibodies. The FaoB polypeptide (SEQ ID NO:26) is not functional in the absence of the FaoA gene product; however, the FaoAB gene product has enzyme activity.

Transgenic lines expressing the FaoA and FaoB complex are obtained by crossing the FaoA and FaoB transgenic lines expressing the individual polypeptides and seeds analyzed by western blotting and enzymes assays as described.

EXAMPLE 6

Transformation of *B. napus* cv. Westar and Analysis of Transgenic Lines

Transformation

The protocol used was adopted from a procedure described by Moloney et al. (1989). Seeds of *Brassica napus* cv. Westar were surface sterilized in 10% commercial bleach (Javex, Colgate-Palmolive Canada Inc.) for 30 min with gentle shaking. The seeds were washed three times in sterile distilled water. Seeds were placed on germination medium comprising Murashige-Skoog (MS) salts and vitamins, 3% sucrose and 0.7% phytagar, pH 5.8 at a density of 20 per plate and maintained at 24° C. in a 16 h light/8 h dark photoperiod at a light intensity of 60–80 $\mu Em^{-2}s^{-1}$ for four to five days.

Each of the constructs, pCGmf124, pCGmf125, pCGmf224, pCGmf225, pCGmf1P2S, and pCGmf2P1S were introduced into *Agrobacterium tumefaciens* strain EHA101 (Hood et al. 1986) by electroporation. Prior to transformation of cotyledonary petioles, single colonies of strain EHA101 harboring each construct were grown in 5 mL of minimal medium supplemented with 100 mg kanamycin per liter, and 100 mg gentamycin per liter for 48 h at 28° C. One milliliter of bacterial suspension was pelletized by centrifugation for 1 min in a microfuge. The pellet was resuspended in 1 mL minimal medium.

For transformation, cotyledons were excised from four-day-old, or in some cases five-day-old, seedlings so that they included approximately 2 mm of petiole at the base. Individual cotyledons with the cut surface of their petioles were immersed in diluted bacterial suspension for 1 s and immediately embedded to a depth of approximately 2 mm in co-cultivation medium, MS medium with 3% sucrose and 0.7% phytagar, enriched with 20 $\mu$M benzyladenine. The inoculated cotyledons were plated at a density of 10 per plate and incubated under the same growth conditions for 48 h. After co-cultivation, the cotyledons then were transferred to regeneration medium, which comprised MS medium supplemented with 3% sucrose, 20 μM benzyladenine, 0.7% phytagar, pH 5.8, 300 mg timentinin per liter, and 20 mg kanamycin sulfate per liter.

After two to three weeks, regenerant shoots were obtained, cut, and maintained on "shoot elongation" medium (MS medium containing 3% sucrose, 300 mg timentin per liter, 0.7% phytagar, and 20 mg kanamycin per liter, pH 5.8) in Magenta jars. The elongated shoots then were transferred to "rooting" medium, which comprised MS medium, 3% sucrose, 2 mg indole butyric acid per liter, 0.7% phytagar and 500 mg carbenicillin per liter. After roots emerged, the plantlets were transferred to potting mix (Redi Earth, W. R. Grace and Co. Canada Ltd.). The plants were maintained in a misting chamber (75% RH) under the same growth conditions. Two to three weeks after growth, leaf samples were taken for neomycin phosphotransferase (NPT II) assays (Moloney et al. 1989). The results are shown in Table 2 below. The data show the number of plants that were confirmed to be transformed.

TABLE 2

NPT II Activity in Transformed Plants

| Constructs | No. of plants | NPTII assayed | NPTII confirmed | No. of plants confirmed transformed |
|---|---|---|---|---|
| [1]pCGmf124 | 47 | 27 | 23 | 33 |
| [2]pCGmf125 | 37 | 28 | 18 | 18 |
| [3]pCGmf224 | 49 | 40 | 30 | 39 |
| [4]pCGmf225 | 52 | 37 | 28 | 34 |
| [5]pCGmf1P2S | 27 | 27 | 21 | 21 |
| [6]pCGmf2P1S | | | | |

[1]pCGmf124 - bean phaseolin regulatory sequences driving FaoA gene
[2]pCGmf125 - soybean oleosin regulatory sequences driving FaoA gene
[3]pCGmf224 - bean phaseolin regulatory sequences driving FaoB gene
[4]pCGmf225 - soybean oleosin regulatory sequences driving FaoB gene
[5]pCGmf192S - bean phaseolin and soybean oleosin regulatory sequences driving FaoA & FaoB genes, respectively
[6]pCGmf2P1S - bean phaseolin and soybean oleosin regulatory sequences driving FaoB & FaoA genes, respectively The fate of the transforming DNA was investigated for sixteen randomly selected transgenic lines. Southern DNA hybridization analysis showed that the FaoA and/or FaoB were integrated into the genomes of the transgenic lines tested.

Approximately 80% of the pmf124 transgenic plants in which the FaoA gene is expressed from the strong bean phaseolin promoter were observed to be male sterile. Clearly high level expression of the FaoA gene from this promoter results in functional expression of the FaoA gene product which impairs seed and/or pollen development. This result was very unexpected, since it was not anticipated that the plant cells would be capable of carrying out the first step in the β-oxidation pathway in the cytosol. This result, however, provides additional applications for expressing β-oxidation genes in plants for male sterility for hybrid production or to prevent the production of seed. It was also note that in a side-by-side comparison with normal transgenic lines, the pmf124 lines produced much higher levels of biomass, presumably due to the elimination of seed development. This phenotype therefore may be useful as a means to increase the amount of green biomass produced per acre for silage, forage, or other biomass crops. Here, the use of an inducible promoter system or recombinase technology could be used to produce seed for planting. Seven of the sterile plants were successfully cross-pollinated with pollen from pmf225 transgenic lines and set seeds.

Northern analysis on RNA from seeds from pmf224 lines containing the phaseolin promoter-FaoB constructs showed a signal indicative of the expected 1.2 kb transcript in all the samples tested except the control. Northern analysis on RNA from seeds from pmf125 lines containing the weak soybean oleolsin promoter-FaoA constructs revealed a transcript of the expected size of 2.1 kb. Western blotting on 300–500 μg of protein from approximately 80% of seeds of pmf125 plants where the FaoA gene is expressed from the relatively weak soybean oleosin promoter were inconclusive, although a weak signal was detected in one transgenic line.

Fatty Acid Analysis

Given the unexpected results indicating a strong metabolic effect of expressing the FaoA gene from the strong bean phaseolin promoter in seeds, the fatty acid profile of the seeds from transgenic lines expressing the FaoA gene from the weak soybean oleosin promoter was analyzed. Seeds expressing only the FaoA gene or also expressing the FaoB gene from the bean phaseolin promoter were examined. The analysis was carried out as described in Millar et al., *The Plant Cell* 11:1889–902 (1998). Seed fatty acid methyl esters (FAMES) were prepared by placing ten seeds of *B. napus* in 15×45-mm screw capped glass tubes and heating at 80° C. in 0.75 mL of 1N methanolic HCl reagent (Supelco, PA) and 10 μL of 1 mg 17:0 methyl ester (internal standard) per mL overnight. After cooling the samples, the FAMES were extracted with 0.3 mL hexane and 0.5 mL 0.9% NaCl by vortexing vigorously. The samples were allowed to stand to separate the phases, and 300 μL of the organic phase was drawn and analyzed on a Hewlett-Packard gas chromatograph.

Fatty acid profile analysis indicated the presence of an additional component or enhanced component in the lipid profile in all of the transgenic plants expressing the FaoA gene SEQ ID NO:24 which was absent from the control plants. This result again proves conclusively that the FaoA gene is being transcribed and translated and that the FaoA polypeptide SEQ ID NO: 27 is catalytically active. This peak also was observed in eleven additional transgenic plants harboring SoyP-FaoA, PhaP-FaoA-SoyP-FaoB, SoyP-FaoA-PhaP-FaoB genes and a sterile (PhaP-FaoA) plant cross-pollinated with SoyP-FaoB. These data clearly demonstrate functional expression of the FaoA gene and that even the very low levels of expression are sufficient to change the lipid profile of the seed. Adapting the methods described herein, one of skill in the art can express these genes at levels intermediate between that obtained with the phaseolin promoter and the soybean oleosin promoter using other promoters such as the *Arabidopsis oleosin* promoter, napin promoter, or cruciferin promoter, and can use inducible promoter systems or recombinase technologies to control when fatty acid oxidation transgenes are expressed.

EXAMPLE 7

Yeast β-oxidation Multi-functional Enzyme Complex

*S. cerevisiae* contains a β-oxidation pathway that proceeds via R-hydroxyacyl CoA rather than the S-3-hydroxyacyl CoA observed in bacteria and higher eukaryotes. The fox2 gene from yeast encodes a hydratase that produces R-3-hydroxyacyl CoA from trans-2-enoyl-CoA and a dehydrogenase that utilizes R-3-hydroxyacyl-CoA to produce β-keto acyl CoAs.

The fox2 gene (sequence shown in SEQ ID NO:1) was isolated from *S. cerevisiae* genomic DNA by PCR in two pieces. Primers N-fox2b and N-bamfox2b were utilized to PCR a 1.1 kb SmaI/BamHI fragment encoding the N-terminal region of Fox2, and primers C-fox2 and C-bamfox2 were utilized to PCR a 1.6 kb BamHI/XbaI fragment encoding the C-terminal Fox2 region. The full fox2 gene was reconstructed via subcloning in vector pTRCN.

N-fox2b fox2 tcc ccc ggg agg agg ttt tta tta tgc ctg gaa att tat cct tca aag ata gag tt (SEQ ID NO:18)

N-bamfox2b fox2 aaggatccttgatgtcatttacaactacc (SEQ ID NO:19)

C-fox2 fox2 gct cta gat agg gaa aga tgt atg taa g (SEQ ID NO:20)

C-bamfox2 fox2 tgacatcaaggatcctttt (SEQ ID NO:21)

The fox1 gene, however, does not possess a β-ketothiolase activity and this activity must be supplied by a second transgene. Representative sources of such a gene include algae, bacteria, yeast, plants, and mammals. The bacterium *Alcaligenes eutrophus* possesses a broad specificity β-ketothiolase gene suitable for use in the methods described herein. It can be readily isolated using the acetoacetyl-CoA thiolase gene as a hybridization probe, as described in U.S. Pat. No. 5,661,026 to Peoples et al. This enzyme also has been purified (Haywood et al., *FEMS Micro. Lett.* 52:91 (1988)), and the purified enzyme is useful for preparing antibodies or determining protein sequence information as a basis for the isolation of the gene.

EXAMPLE 8
Plant β-Oxidation Gene

The DNA sequence of the cDNA encoding β-oxidation tetrafunctional protein, shown in SEQ ID NO:4, can be isolated as described in Preisig-Muller et al., *J. Biol. Chem.* 269:20475–81 (1994). The equivalent gene can be isolated from other plant species including Arabidopsis, Brassica, soybean, sunflower, and corn using similar procedures or by screening genomic libraries, many of which are commercially available, for example from Clontech Laboratories Inc., Palo Alto, Calif., USA. A peroxisomal targeting sequence P-R-M was identified at the carboxy terminus of the protein. Constructs suitable for expressing in the plant cytosol can be prepared by PCR amplification of this gene using primers designed to delete this sequence.

EXAMPLE 9
Expression of PHA Biosynthetic Pathways in Seeds of *Brassica napus*

Synthesis of PHAs via β-oxidation requires a reductase for the reduction of acetoacetyl-CoA and a PHA synthase for subsequent polymerization of the resulting hydroxyacyl-CoA molecules. To express FaoA, FaoB, reductase and synthase in plants, the promoters from bean phaseolin (pha), soybean oleosin (soy) and Arabidopsis oleosin (Ara) were used to express the bacterial genes in a seed-specific manner. In addition, a constitutive parsley ubiquitin (ubiq) regulatory sequence was used to express the synthase gene.

Seed-specific-FaoA and FaoB Constructs

For seed-specific expression of the bacterial FaoA, FaoB, reductase and synthase genes, and constitutive expression of the synthase gene, plant promoter-terminator cassettes were constructed. All the expression cassettes were constructed in pBluescript before subdloning in Agrobacterium-based plant transformation vector.

The *Pseudomonas putida* FaoA and FaoB genes were amplified from plasmid pMFX3, cloned into pUC19 and pBluescript respectively, and sequenced. Functional assays using the amplified FaoA (mf1) gene performed at Metabolix Inc. found the PCR fragment to contain coding sequence which specifies biological activities for hydratase, dehydrogenase and thiolase. The FaoA (mf1) and FaoB (mf2) PCR fragments were inserted into an expression cassette containing phaseolin (pSBS2024), soybean oleosin (pSBS2025) or Arabidopsis oleosin (pSBS2038) regulatory sequences shown.

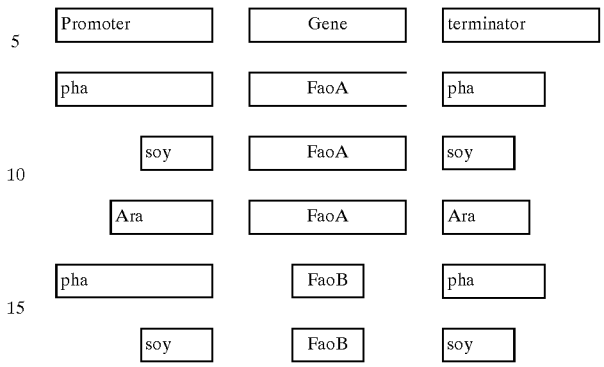

The seed-specific expression cassettes containing either the FaoA or FaoB genes were inserted into the plant transformation vectors pCGN1559 (see FIG. 7) and pSBS2004. pCGN1559 contains CaMV 35S promoter driving expression of the nptII gene (which confers resistance to the antibiotic, kanamycin) while pSBS2004 contains a parsley ubiquitin promoter driving the PAT gene which confers resistance to phosphinothricine. Plasmids, pCGmf1P2S, pCGmf2P1S and PCGmf1A2P contain both FaoA and FaoB in the same binary vector (see FIG. 7).

Seed-specific Arabidopsis-Reductase Construct

A plasmid pTRCN c.v. phaB was used as a template in an amplification reaction to obtain a 790 bp fragment encoding the acetoacyl CoA reductase from *Chromatium vinosum*. The PCR fragment was cloned into pBluescript and sequence analysis confirmed identity to the original bacterial gene. The consumption of NADH measured at 340 nm in the presence of acetoacetyl CoA showed that the activity of the gene product of the amplified fragment pTRCNRBSH-Rd108 gave similar activity, within the error of the assay, as the starting construct pTRCN c.v. phaB. The reductase fragment was cloned into pSBS2038 under the control of the Arabidopsis oleosin promoter to obtain plasmid pMI5006 shown below.

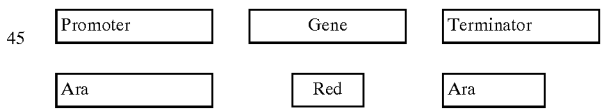

Figure 7A:
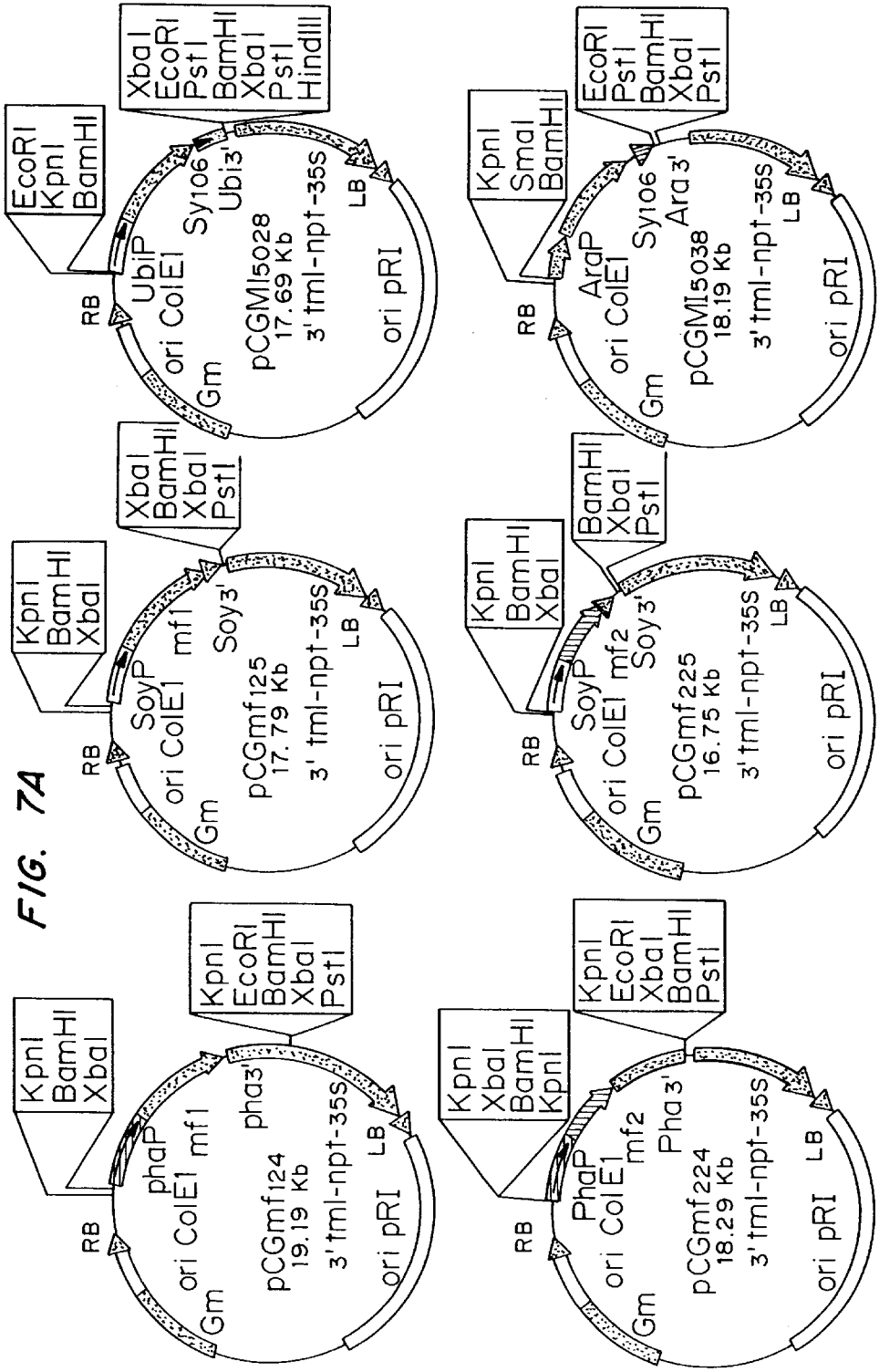
FIGS. 7A and 7B is a schematic showing plasmid constructs pCGmf1124, pCGmf125,pCGMI5028, pCGmf224, pCGmf225, pCGMI5038, pCGmf1P2S, pCGmf2P1S, pCGMI5006, pCGmf138, pCGmf1A2P, and pCGmf5034.
Figure 7B:
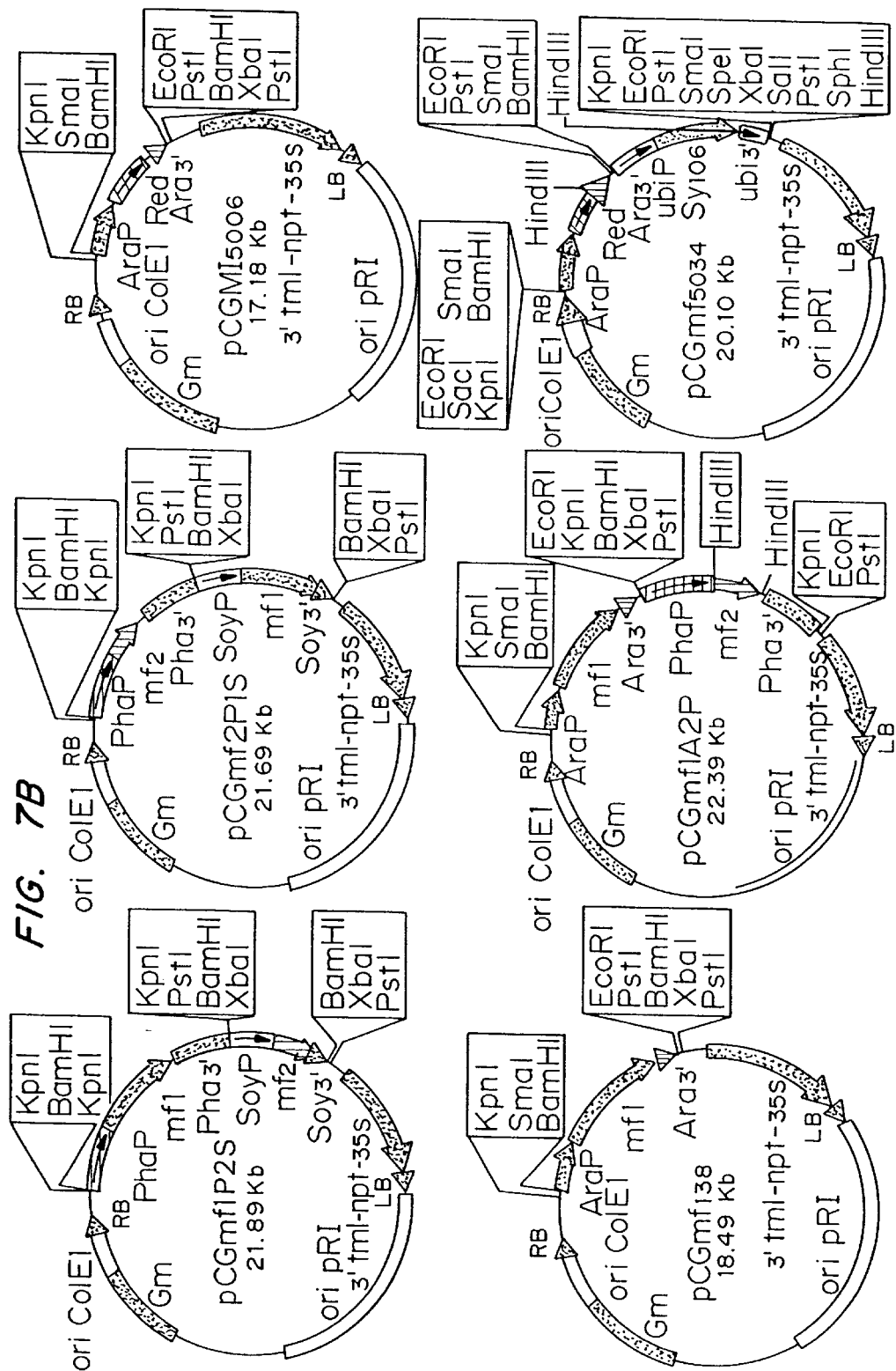

The seed-specific cassette for the expression of the reductase gene was cloned into the binary vector pCGN1559 to create plasmid pCGMI5006 for transformation into *B. napus* (see FIG. 7).

| Construct name | Activity (U/mg) |
|---|---|
| pTRCNRBSH-Rd108 | 3.79 +/− 0.29 |
| pTRCN C.v. phaB | 3.40 +/− 0.46 |
| pTRCNRBSH | 0.19 +/− 0.01 |

Seed-specific and Constitutive Synthase Constructs

Similarly, the plasmid $PMSXp_{B4}C5_{cat}$ containing a fragment encoding a hybrid *Pseudomonas oleovorans/Zoogloea ramigera* synthase was used as a template to amplify a 1.79 kb fragment. The PCR fragment was cloned into pUC19 and sequenced. Functional analysis was performed at Metabolix Inc. by transforming the amplified fragment into an *E. coli* strain already expressing reductase and thiolase genes. This was grown in LB/glucose medium and was shown to make PHA. GC analysis of the whole *E. coli* cell pellet showed the presence of PHA whereas a control strain without the amplified fragment did not. The amplified fragment was inserted into the seed-specific promoter-terminator cassette pSBS2038 resulting in plasmid pMI5038 as shown.

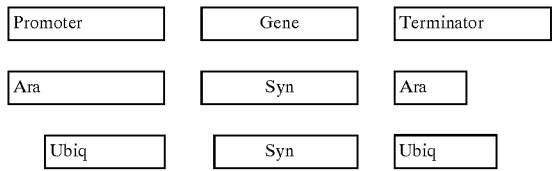

For the expression of the synthase gene in a constitutive manner, the amplified fragment was cloned into the plasmid pSBS2028 containing the parsley ubiquitin promoter-terminator regulatory sequences also shown above. The Arabidopsis oleosin promoter-synthase and ubiquitin promoter-synthase genes were subsequently cloned into the binary vector pCGN1559 to generate plasmids pCGMI5038 and pCGMI5028 respectively (see FIG. 7) for transformation. Plasmid pMI5034 contains both synthase and reductase coding sequences under the regulatory control of ubiquitin and oleosin promoters respectively.

FaoA Fusion to GUS Reporter Construct

To demonstrate that the FaoA and FaoB genes are transcribed and translated in a plant, a translational fusion with the *E. coli* betaglucuronidase (GUS) gene was made. The full length amplified FaoA (mf1) gene was fused in frame to GUS and the resulting fragment was inserted into the expression cassette pSBS2038 which contained the Arabidopsis oleosin regulatory sequences.

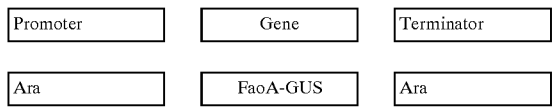

The final plasmid pGUSmf138 was used in biolistics experiments. To establish whether the FaoA gene would accumulate as a fusion protein in plants, the chimaeric Arabidopsis-FaoA fragment was cloned into the binary vector pCGN1559 and the resulting plasmid, pCGmfG138 was used to transform *Brassica napus*.

Plant Transformation

Agrobacterium-based binary vectors were used to transform cotyledons of 4 to 5 day old seedlings of *Brassica napus* cv. Westar. Table 3 below shows the various constructs used for transformation and the number of transformed plants generated. Each construct comprises a particular plant regulatory sequence and the bacterial coding sequences within the binary vector pCGN1559. The number of transformed plants are indicated. Maps of the various constructs are also indicated in FIG. 7. Surviving transgenic plants of pha-FaoA were all sterile and unable to set seeds. Six out of sixteen transgenic plants from the pha-FaoA/soy-FaoB construct and two of soy-FaoA/pha-FaoB plants were also sterile.

TABLE 3

Transformation Constructs & Number of Transformed Plants

| Construct name | Description (promoter-bacterial gene) | Number of transformed plants |
|---|---|---|
| pCGmf124 | pha-FaoA | 33 |
| pCGmf125 | soy-FaoA | 18 |
| pCGmf138 | Ara-FaoA | 6 |
| pCGmf224 | pha-FaoB | 39 |
| pCGmf225 | soy-FaoB | 34 |
| pCGmf1P2S | pha-FaoA-soy-FaoB | 16 |
| pCGmf2P1S | soy-FaoA-pha-FaoB | 9 |
| pCGmf1A2P | Ara-FaoA-pha-FaoB | 9 |
| PCGmfG138 | Ara-FaoA-GUS | 5 |
| PCGMI5006 | Ara-Red | 10 |
| PCGMI5028 | ubiq-Syn | 10 |
| PCGMI5038 | Ara-Syn | 6 |
| PCGMI5034 | ubiq-Syn-Ara-Red | 2 |

Promoters: *Arabidopsis oleosin* (Ara); *Soybean oleosin* (soy); Phaseolin (pha); and Ubiquitin (ubiq);
Genes: FaoA and FaoB encode bacterial fatty acid β-oxidation multifunctional complex Red and Syn encode reductase and synthase respectively

EXAMPLE 10

Analysis of Transgenic Plants

All the transgenic plants showed normal development except pha-FaoA plants which were found to exhibit morphological changes. The plants were sterile and therefore unable to set seed. They showed vigorous growth and produced more biomass. Characterization of the transforming DNA by Southern blot showed that the FaoA gene had stably integrated into plant genome. Transient expression studies using a GUS reporter gene fused to FaoA demonstrated that the FaoA gene can be transcribed and translated in plants. Coexpression of both FaoA and FaoB in embryos also suggests the formation of a more stable complex. This is supported by transient expression studies where GUS activity in a GUS-FaoA fusion increased more than two fold when FaoB is coexpressed. Expression of FaoB was evident by the presence of the transcript and polypeptide in transgenic plants. The expression of FaoA in plants was further demonstrated by the detection of the transcript and polypeptide in plants transformed with a construct containing the Arabidopsis oleosin promoter regulating the FaoA gene. Changes in fatty acid profiles of total seed lipid content in addition to an alteration in morphology is evidence of functional expression of FaoA in transgenic plants. Northern and Western blot analysis also demonstrated transcription and translation of the reductase and synthase genes in transgenic plants.

Morphological Changes in FaoA- and FaoB-expressing Plants

Expression of the FaoA transgene under the control of the phaseolin promoter caused unexpected morphological changes in the transgenic plants. The plants developed normally until flowering where the FaoA-expressing plants were found to be male sterile. This suggests that the phaseolin promoter regulating the FaoA gene was active during male gametogenesis. It has been demonstrated that phaseolin promoter is active during microsporogenesis in transgenic tobacco (van der Geest, et al., *Plant Physiol.* 109:1151–58 (1995)). The plants visibly showed vigorous growth with a bushy appearance and produced more biomass when compared with plants transformed with either the binary vector alone (pCGN1559 control) or containing soy-FaoA, pha-FaoB or soy-FaoB constructs:. This altered morphology is presumably caused by reduced fertility as these plants were unable to set seed. It should be noted that seven of the male sterile plants were successfully crossed with pollen from soy-FaoB transgenic plants. It is likely that the functional over-expression of the Fa.A gene product has caused an alteration in a fundamental process required for the normal development of the plant. Transgenic plants carrying the pha-FaoA/soy-FaoB and soy-FaoA/pha-FaoB constructs on the other hand showed normal growth. It is therefore hypothesized that the accumulation of detrimental substrates resulting from the overexpression of functional FaoA may be converted to benign metabolites when active FaoB protein is present.

Analysis of the Transgene in the Plant Genome

Successful gene transfer was confirmed by Southern blot analysis of total genomic isolated from leaves of the transgenic plants that had been digested with Pvu II restriction enzyme. The enzyme cuts once within the FaoA gene, the nptII gene and outside of the promoter sequence. Hybridization analysis using a radiolabelled FaoAB gene probe demonstrated the stable integration of the FaoA gene. In transgenic pha-FaoA plants (No. 15 and 44), the probe hybridized to the unexpected 2.4 and 2.8 kb fragments. The DNA containing soy-FaoA fragment in transgenic plants 69, 76, and 85 also appears to have inserted stably, generating 1.4 and 2.2 kb fragments. The hybridization pattern observed in plant number 82 seems to indicate that in this transformant, the DNA had integrated into more than one site. In transgenic plant 67, there appears to have been a rearrangement of the inserting DNA. Hybridization analysis of transgenic pha-FaoB plants (111 and 121) also showed stable integration of the sequence. The autoradiogram shows hybridization of the $^{32}$P-labelled FaoAB gene probe to the expected 2.1 and 2.3 kb fragments. In transgenic plants that harbor both FaoA and FaoB genes under the control of phaseolin and soybean regulatory sequences, three hybridizing fragments (0.9, 2.8, and 3.9 kb for pha-FaoA/soy-FaoB, and 2.1, 2.2, and 3.2 kb for soy-FaoA/pha-FaoB plants) were expected with the probe. The hybridizing bands in transgenic plant numbers 202 (pha-FaoA/soy/FaoB) and 252 (soy-FaoA/pha-FaoB) correctly indicated the expected DNA size fragments. The probe shows some nonspecific hybridization at the stringency used, as some hybridization is also seen in the control (plant transformed with pCGN1559).

Analysis of MRNA and Protein Accumulation

Developing transgenic seeds were harvested at various stages and analyzed for the expression of the bacterial FaoA and FaoB genes using Northern and Western analysis. Northern blot analysis was performed on 30 μg of total seed RNA using radiolabelled DNA fragments representing the coding sequence of the bacterial genes. For immunodetection, extracts of total seed protein were size-fractionated on 10–12% polyacrylamide-SDS gels and transferred to PVDF membrane. Antibodies raised in rabbits against the bacterial FaoA or FaoB protein, and goat anti-rabbit IgG conjugated to horseradish peroxidase were used to visualize the related polypeptides using chemiluminescence ECL immunodetection.

Northern and Western blot analysis were performed on seed extracts from soy-FaoA transgenic plants which showed normal growth. A weak signal of the related transcript was detected in one of four transgenic plants analyzed. The presence of the encoded polypeptide was tested by Western immunoblot analysis. In the transgenic plants analyzed, the anti-FaoA antibody did not detect the polypeptide. The presence of MRNA transcript from seeds of pha-FaoB (Plant No. 101, 102, 103, 111, and 121) was also analyzed by Northern hybridization. An oleosin probe was used as an internal standard to hybridize to the blot before it was partially stripped and reprobed with the radiolabelled FaoAB gene fragment. Hybridizing transcripts of expected size were detected in five transgenic plants and absent from control plant as well as FaoA-expressing (No. 22 and 77) plants. Immunoblot analysis of FaoB-related polypeptide in plants showed that in the crude protein extract of a mf111 plant, the anti-FaoB antibody cross-reacted with a polypeptide of approximately 43 kD similar in molecular weight to the FaoB standard. The extra non-specific hybridizing band in all samples may represent seed oilbody protein. No polypeptide was detected in one-fifth of plants analyzed from the same transgenic line. In addition, the anti-FaoB antibody did not bind to related polypeptide in samples tested from the soy-FaoB plants. It is likely that the related-FaoB polypeptide is unable to accumulate as the protein is normally stabilized in vivo by the presence of the FaoA protein as demonstrated in bacterial systems. In some transgenic seeds of soy-FaoA/pha-FaoB analyzed, hybridizing transcripts were detected for FaoB but not FaoA. However, the related polypeptide could not be detected by Western blot analysis.

GC Analysis

Although the expression of the soy-FaoA fragment could not be detected by Northern and Western blot analysis, the morphological alteration of transgenic plants resulting from pha-FaoA expression was indirect evidence for the functional expression of an FaoA gene product. Since FaoA is a key component in oxidation of fatty acids, a profile of total seed lipid from soy-FaoA and control transgenic plants was analyzed. Fatty acid methyl esters were prepared according to Kunst, et al., "Fatty acid elongation in developing seeds of *Arabidopsis thaliana.*" *Plant Physiol. Biochem.* 30:425–34 (1992) and analyzed by gas chromatography. The chromatogram shows an enhanced peak of a low molecular weight fatty acid (arrowed) which was absent in the control transgenic plant. This enhanced peak was also observed in a plant transformed with the pha-FaoA/soy-FaoB construct. The same peak was observed in eleven other transgenic plants including a male-sterile phas-FaoA plant fertilized with pollen from soy-FaoA plant. The results support the conclusion that the FaoA polypeptide is functional and perturbs an essential metabolic process. A GC-MS analysis identified the peak as pentanoic acid which would be an unusual cleavage product of a functional FaoA.

Transient Assay of Expression of the FaoA and FaoB Genes in Embryos

It is clear from the analysis presented that the pha-FaoB transcript accumulates and is translated into its polypeptide. However, in an effort to demonstrate unequivocally that FaoA is indeed transcribed and translated, a translational fusion with GUS at the C-terminus was made. The hypothesis was that if the reporter enzyme GUS accumulates, then the FaoA gene must have been transcribed and translated. From the literature, it is known that FaoA and FaoB can interact to form a stable complex in bacterial systems (Imamura, et al., "Purification of the multienzyme complex for fatty acid oxidation from *Pseudomonas fragi* and reconstitution of the fatty acid oxidation system" *J. Biochem.* 107: 184–89 (1990)). In order to test this hypothesis in plants, both FaoA and FaoB were expressed simultaneously in a transient manner. An Ara-FaoA-GUS construct was used in this study in addition to the pha-FaoB construct. The oilseed embryos used in this study were from *Brassica napus* L. cv Topas and *Linum usitatissimum* (flax) cv. MacGregor. Microspore embryos were obtained from *B. napus* while zygotic embryos were isolated from flax. Particle bombardment of embryos was essentially as described in Abenes, et al., "Transient expression and oil body targeting of an Arabidopsis oleosin-GUS reporter fusion protein in a range of oilseed embryos" *Plant Cell Reports* 17:1–7 (1997). Tables 4 and 5 show GUS fluorimetric activities in the different fractions of embryo extracts. The GUS activity of Ara-GUS (pGN1.1) in microspore-derived embryos was at least eight times the background (pSBS2105) while the activity of Ara-FaoA-GUS (pmfG138) was more than double the background activity (Table 4). When embryos were co-bombarded with pmfG138 (Ara-FaoA-GUS) and pmf224 (pha-FaoB) DNA in equal amounts, the specific activity of GUS was observed to be more than three times that of background activity. A comparison of the Ara-FaoA-GUS activity to Ara-FaoA-GUS:pha-FaoB showed that the latter value was almost double the former value when the background specific activity was subtracted. It appears that the co-expression of both FaoA and FaoB contributed to the increase in activity. This result was further confirmed when zygotic embryos were bombarded with the set of plasmids described in Table 4 using microspore embryos. The data describes not only the use of microspore and zygotic embryos to express FaoA and FaoB genes, but also stresses the importance of the expression of these genes in different plant species.

TABLE 4

GUS activity levels in total homogenate of microspore embryos from *Brassica napus* L. Cv. Topas.

| Construct name | Description | GUS activity (pmol MU/min) | Specific activity (activity/mg prt) |
|---|---|---|---|
| pSBS2105 | pBluescript-based plasmid | 30.5 | 7.78 |
| pGN1.1 | Ara-GUS | 256.5 | 53.1 |
| pmfG138 | Ara-FaoA-GUS | 69 | 17.7 |
| pmfG138: pmf224 | Ara-FaoA-GUS: pha-FaoB | 85 | 29.1 |

The promoter used to regulate the expression of GUS and FaoA-GUS was from the Arabidopsis (Ara) oleosin gene. The phaseolin (pha) promoter was used to regulate FaoB expression.

Table 5 shows the levels of GUS activity in oilbody and supernatant (OS) and supernatant (SN) fractions. The recorded activity in the OS fraction was double the activity in SN fraction. It appears that some amount of GUS is also associated with oilbodies. This is most likely due to the hydrophobic nature of GUS and not the FaoA or FaoB protein. In both fractions, there was an increase in GUS activity when the Ara-FaoA-GUS and pha-FaoB fragments were co-expressed in a ratio of 1:1 over the Ara-FaoA-GUS. The activity increases further when the ratio of plasmid pmfG138:pmf224 DNA used was 1:3 (Table 5). The results obtained from transient assays of zygotic flax embryos confirmed the observations noted in Table 4 when Brassica embryos were used. It is clear that the FaoA gene is transcribed and translated and that the product of FaoB gene expression increases the activity of the FaoA-GUS fusion protein. The effect of FaoB most likely occurs by forming a complex with FaoA and stabilizing the FaoA domain within the FaoA-Gus fusion protein.

TABLE 5

GUS activity levels in total homogenate (OS, oilbody fraction and supernatant) and supernatant (SN) of zygotic embryos from flax.

| Fraction | Construct name | Description | GUS activity (pmol MU/min) | Specific activity (activity/mg prt) |
|---|---|---|---|---|
| OS | pSBS2105 | pBluescript-based | 7.40 | 1.36 |
|  | pGN1.1 | Ara-GUS | 656.92 | 113.20 |
|  | pmfG138 | Ara-FaoA-GUS | 265.14 | 43.30 |
|  | pmfG138: pmf224 (1:1) | Ara-FaoA-GUS:pha-FaoB | 386.26 | 52.84 |
|  | pmfG138: pmf224 (1:3) | Ara-FaoA-GUS:pha-FaoB | 440.21 | 78.98 |
| SN | pSBS2105 | pBluescript-based | 2.55 | 0.47 |
|  | pGN1.1 | Ara-GUS | 373.83 | 64.47 |
|  | pmfG138 | Ara-FaoA-GUS | 132.38 | 21.62 |
|  | pmfG138: pmf224 (1:1) | Ara-FaoA-GUS:pha-FaoB | 174.54 | 23.88 |
|  | pmfG138: pmf224 (1:3) | Ara-FaoA-GUS:pha-FaoB | 214.07 | 38.41 |

The Arabidopsis oleosin promoter (Ara) was used to regulate the expression of GUS and FaoA-GUS and a phaseolin (pha) regulatory sequence was used to drive the expression of FaoB.

EXAMPLE 11

Comparison of Promoters

Using the phaseolin promoter as a regulatory sequence to express the FaoA gene proved lethal to the normal development of transgenic *B. napus* plants, which indicates expression of a functional FoaA. Furthermore, the soybean oleosin promoter was comparatively weaker in expressing either the FaoA or FaoB transgenes. In an effort to express the FaoA transgene in a seed-specific manner, a relatively strong Arabidopsis oleosin promoter was used. An Ara-FaoA construct was assembled in plasmid pCGN1559 and used to transform *B. napus*. Plant transformation was also initiated with the Ara-Red, Ara-Syn, and ubiq-Syn constructs. The following analyses were conducted on some of the transgenic plants obtained.

Analysis of Integration of Chimeric Arabidopsis-FaoA DNA Fragment

A Southern blot was prepared from 30 $\mu$g of total plant genomic DNA digested with EcoRV. A radiolabelled coding sequence of the FaoA gene was used as a probe for hybridization. There was successful integration of the transgene into the plant genome in four of the samples analyzed. The number of hybridizing fragments indicate one or two copies of the insertion within the plant genome. The probe did not hybridize to DNA from the control plant.

Analysis of Expression of the FaoA Transgene in *B. napus*

A Northern blot was prepared using 30 $\mu$g of total RNA extracted from transgenic seeds. A $^{32}$P-labelled FaoA gene probe hybridized to the related transcript of expected size in transgenic plants. No hybridization was observed with RNA from the control plant. For immunodetection, total seed protein extracts were size-fractionated on 10–12% polyacrylamide-SDS gels and transferred to PVDF membrane. Antibodies raised in rabbits against the bacterial FaoA, and FaoB protein, and goat anti-rabbit IgG conjugated to alkaline phosphatase (AP), were used to visualize the related polypeptides by using NBT and BCIP as AP substrates. Immunoblotting of 300 $\mu$g of total seed protein prepared from Ara-FaoA plants with an anti-FaoAB antibody showed that the FaoA gene was both transcribed and translated in B. napus. The cross-reacting polypeptide from the protein extract had the same molecular mass as the purified FaoA protein standard. No immunoreaction to a related polypeptide was detected in control plant extracts. Nonspecific hybridization of the antibody with seed storage proteins, present in high amounts in the later development stages of *B. napus,* account for the signal seen in all plants. The results clearly demonstrate that the *Pseudomonas putida* FaoA gene is expressed in *B. napus* plants when the Arabidopsis oleosin promoter is used to regulate expression.

Analysis of FaoA/FaoB-expressing Transgenic Plants

Northern and Western blot analysis were also performed on transgenic seeds from plants transformed with a construct containing both FaoA and FaoB genes on the same binary vector. FaoA and FaoB were under the regulation of Arabidopsis oleosin and phaseolin promoters respectively. Autoradiography shows the respective transcripts in both genes from plant number 507; however, no transcripts were detected in control and three other plants. In Western blot analysis of total seed protein from plant number 504 and 507, only the FaoA polypeptide could be detected. Although, a transcript could be detected with the FaoB probe, the related polypeptide was not detected in the Western analysis using the anti-FaoAB antibody.

Analysis of Expression of the Reductase Transgene in *B. napus*

In order to determine if the reductase gene was expressed in transgenic plants, the cloned reductase coding sequence was radiolabelled and used as a probe in Northern blot hybridization. Autoradiography shows that the probe did not hybridize to RNA from the control plant. In contrast, mRNA from two of the three transgenic plants analyzed, hybridized to the reductase gene probe. To examine the translational product resulting from the transcription of the reductase gene, a Western blot was prepared with 300 μg of protein extract in all four samples analyzed and the polypeptide co-migrated with the purified bacterial reductase protein standard. There was no immunodetection of a related polypeptide in the control plants. The extra nonspecific hybridizing band may represent accumulating oilbody protein in mature seeds. This result suggests that the bacterial reductase gene is transcribed, and translated in *B. napus* plant.

Expression of the Synthase Gene in Transgenic Plants

To examine the expression of the hybrid synthase in transgenic plants in a constitutive as well as seed-specific manner, total RNA was isolated from seeds. Thirty micrograms of RNA blotted onto nylon membrane was hybridized with a $^{32}$P-labelled synthase gene. Related transcripts from two of the three ubiq-syn transgenic plants showed cross-hybridization with the complementary probe while no signal was observed in the control plant. Although the gene was transcribed as revealed by the Northern analysis, the related polypeptide could not be detected by Western blot analysis of protein extracts from leaves as well as seeds using the anti-synthase antibody. However, a similar transcript was detected on Northern blot of total RNA isolated from Ara-syn transgenic plants and the related polypeptide was immunodetected with the anti-synthase antibody. The related polypeptide co-migrated with the purified synthase and showed the same degradation products. In addition, a low molecular weight cleavage product was observed in the transgenic lines analyzed.

Synthesis of Polymer in Embryos

As previously demonstrated in this study, the β-oxidation enzymes FaoA and FaoB can be transcribed and translated in embryo cells. In an attempt to synthesize PHA via β-oxidation of fatty acids in a transient fashion, flax zygotic embryos were co-bombarded with the Ara-FaoA, pha-FaoB, Ara-Red, and Ara-Syn constructs. A further biolistic experiment was performed on another set of embryos with either the Ara-Syn or gold particles alone. Butanolysis of embryos using PHB as internal standard in the solvents ethanol, methanol, chloroform ,and hexane was performed at Metabolix Inc. GC analysis of the chromatograms from ethanol and methanol soluble fractions did not show any differences between samples. However, in the chloroform and hexane soluble fractions, enhanced peaks at about 16.5 min in samples 2 (Ara-Syn) and 3 (Ara-FaoA, pha-FaoB, Ara-Red and Ara-Syn) were observed. The peaks were not present in sample 1 which was bombarded with gold-coated particle alone. The GC analysis could not detect PHB which is extractable in chloroform in any of the samples. Some conclusions drawn from this analysis suggest that if there was PHB in the samples, it would be less than 0.3% of the total cell dry weight of the samples analyzed, because 0.24 mg of PHB standard could be detected on the GC. Secondly, the unidentified peaks are chloroform and hexane extractable and a medium chain-length polymer would be expected to be extractable in both solvents. GC-MS analysis can be performed to identify these compounds. It should be noted that these peaks could not be found in GC analysis of insoluble fractions or residual cell matter.

Modifications and variations of the present invention will be obvious to those of skill in the art from the foregoing detailed description. Such modifications and variations are intended to come within the scope of the following claims.

We claim:

1. A method for manipulating the metabolism of a plant, comprising introducing heterologous nucleic acid sequences encoding fatty acid oxidation enzymes into plant cells under conditions wherein the nucleic acid sequences are integrated into the plant genome and the enzymes are expressed in the cytosol or optionally subsequently transported into the plastids of the plant, wherein the genes encode enzymes selected from the group consisting of enzymes converting acyl CoA thioester to trans-2-enoyl-CoA, hydrating trans-2-enoyl-CoA to R-3-hydroxy acyl CoA, hydrating trans-2-enoyl-CoA to S-3-hydroxy acylCoA, epimerizing S-3-hydroxyacyl-CoA to R-3-hydroxyacyl-CoA, oxidizing 3-hydroxyacyl CoA to form beta-keto acyl CoA, and thiolyzing beta-keto acyl CoA to yield acetyl CoA.

2. The method of claim 1 wherein the fatty acid oxidation enzymes are expressed from genes selected from the group consisting of bacterial, yeast, fungal, plant, and mammalian genes.

3. The method of claim 2 wherein the fatty acid oxidation enzymes are expressed from nucleic acid sequences from bacteria selected from the group consisting of Escherichia, Pseudomonas, Alcaligenes, and Coryneform.

4. The method claim 3 wherein the nucleic acid sequences are *Pseudomonas putida* faoAB.

5. The method of claim 1 further comprising
    expressing nucleic acid sequences encoding enzymes selected from the group consisting of polyhydroxyalkanoate synthases, acetoacetyl-CoA reductases, β-ketoacyl-CoA thiolases, and enoyl-CoA hydratases.

6. The method of claim 1 wherein the enzymes contain a plastid targeting signal sequence.

7. A DNA construct for use in a method of manipulating the metabolism of a plant cell comprising, in phase,
    (a) a promoter functional in a plant;
    (b) a DNA sequence encoding at least one fatty acid oxidation enzyme activity, wherein the nucleic acid sequences encode enzymes selected from the group consisting of enzymes converting acyl CoA thioester to trans-2-enoyl-CoA, hydrating trans-2-enoyl-CoA to R-3-hydroxy acyl CoA, hydrating trans-2-enoyl-CoA to S-3-hydroxy acylCoA, epimerizing S-3-hydroxyacyl-CoA to R-3-hydroxyacyl-CoA, oxidizing 3-hydroxyacyl CoA to form beta-keto acyl CoA, and thiolyzing beta-keto acyl CoA to yield acetyl CoA; and (c) a polyadenylation sequence, functional in plants.

8. The DNA construct of claim 7 wherein the promoter is a seed specific promoter.

9. The DNA construct of claim 8 wherein the seed specific promoter is selected from the group consisting of napin promoter, phaseolin prormoter, oleosin promoter, 2S albumin promoter, zein promoter, β-conglycinin promoter, acyl-carrier protein promoter, and fatty acid desaturase promoter.

10. The DNA construct of claim 7 wherein the promoter is a constitutive promoter.

11. The DNA construct of claim 7 wherein the promoter is selected from the group consisting of CaMV 35S promoter, enhanced CaMV 35S promoter, and ubiquitin promoter.

12. A transgenic plant or part thereof comprising heterologous nucleic acid sequences encoding fatty acid oxidation enzymes which are expressed in the cytosol or optionally subsequently transported into the plastids of the cells of the plant, wherein the genes encode enzymes selected from the group consisting of enzymes converting acyl CoA thioester to trans-2-enoyl-CoA, hydrating trans-2-enoyl-CoA to R-3-hydroxy acyl CoA, hydrating trans-2-enoyl-CoA to S-3-hydroxy acylCoA, epimerizing S-3-hydroxyacyl-CoA to R-3-hydroxyacyl-CoA, oxidizing 3-hydroxyacyl CoA to form beta-keto acyl CoA, and thiolyzing beta-keto acyl CoA to yield acetyl CoA.

13. The transgenic plant or part thereof of claim 12 wherein the fatty acid oxidation enzymnes are expressed from nucleic acid sequences selected from the group consisting of bacterial, yeast, fungal, plant, and mammalian.

14. The transgenic plant or part thereof of claim 13 wherein the fatty acid oxidation enzymes are expressed from nucleic acid sequences from bacteria selected from the group consisting of Escherichia, Pseudomonas, Alcaligenes, and Coryneform.

15. The transgenic plant or part thereof of claim 14 wherein the nucleic acid sequences are *Pseudomonas putida* faoAB.

16. The transgenic plant or part thereof of claim 13, wherein the fatty acid oxidation enzymes contain a plastid targeting signal sequence.

17. The transgenic plant of part thereof of claim 12 further comprising nucleic acid sequences encoding enzymes selected from the group consisting of polyhydroxyalkanoate synthases, acetoacetyl-CoA reductases, β-ketoacyl-CoA thiolases, and enoyl-CoA hydratases.

18. The transgenic plant or part thereof of claim 12 wherein the plant is selected from the group consisting of Brassica, maize, soybean, cottonseed, sunflower, palm, coconut, safflower, peanut, mustards, flax, tobacco, and alfalfa.

19. A transgenic plant or part thereof comprising a DNA construct comprising, in phase, (a) a promoter functional in a plant;

(b) a structural DNA sequence encoding at least one fatty acid oxidation enzyme selected from the group consisting of enzymes converting acyl CoA thioester to trans-2-enoyl-CoA, hydrating trans-2-enoyl-CoA to R-3-hydroxy acyl CoA, hydrating trans-2-enoyl-CoA to S-3-hydroxy acylCoA, epimerizing S-3-hydroxyacyl-CoA to R-3-hydroxyacyl CoA, oxidizing 3-hydroxyacyl CoA to form beta-ketoacyl CoA, and thiolyzing beta-keto acyl CoA to yield acetyl CoA; and (c) a polyadenylation sequence, functional in plants.

20. The transggenic plant or part thereof of claim 19 wherein the promoter is a seed specific promoter.

21. The transgenic plant or part thereof of claim 20 wherein the seed specific promoter is selected from the group consisting of napin promoter, phaseolin promoter, oleosin promoter, 2S albumin promoter, zein promoter, β-conglycinin promoter, acyl-carrier protein promoter, and fatty acid desaturase promoter.

22. The transgenic plant or part thereof of claim 19 wherein the promoter is a constitutive promoter.

23. The transgenic plant or part thereof of claim 19 wherein the promoter is selected from the group consisting of CaMV 35S promoter, enhanced CaMV 35S promoter, and ubiquitin promoter.

24. A method to produce R-3-hydroxyacyl CoA from trans-2-enoyl-CoA and β-keto acyl CoA from R-3-hydroxyacyl-CoA in a plant comprising introducing a heterologous nucleic acid sequence encoding fox2 into the cells of the plant wherein the heterologous nucleic acid sequence is integrated into the genome of the cells of the plant and wherein the heterologous nucleic acid sequence encodes an enzyme that is expressed in the cytosol or optionally subsequently transported into the plastids of the plant.

25. A method for manipulating the metabolism of a plant, comprising introducing a heterologous nucleic acid sequence encoding a fatty oxidation enzyme into the cells of the plant under conditions wherein the heterologous nucleic acid sequence is integrated into the genome of the cells of the plant and the enzyme is expressed in the cytosol or optionally subsequently transported into the plastids of the cells of the plant, wherein the heterologous nucleic acid sequence encodes a fox1 enzyme.

26. A method for manipulating the metabolism of a plant, comprising introducing heterologous nucleic acid sequences encoding fatty acid oxidation enzymes into the cells of the plant under conditions wherein the heterologous nucleic adid sequences are integrated into the plant plastid genome and the enzymes are expressed in the plastids of the plant, wherein the heterologous nucleic acid sequences encode enzymes selected from the group consisting of enzymes converting acyl CoA thioester to trans-2enoyl-CoA, hydrating trans-2-enoyl-CoA to R-3-hydroxy acyl CoA, hydrating trans-2-enoyl-CoA to S-3-hydroxy acylCoA, epimerizing S-3-hydroxyacyl-CoA to R-3-hydroxyacyl-CoA, oxidizing 3-hydroxyacyl CoA to form beta-keto acyl CoA, and thiolyzing beta-keto acyl CoA to yield acetyl CoA.

* * * * *